US007662824B2

(12) United States Patent
Leonard et al.

(10) Patent No.: US 7,662,824 B2
(45) Date of Patent: Feb. 16, 2010

(54) ACYLHYDRAZONES AS KINASE MODULATORS

(75) Inventors: Kristi Leonard, West Chester, PA (US); Tianbao Lu, Churchville, PA (US); Robert W. Tuman, Chalfont, PA (US); Dana L. Johnson, Upper Black Eddy, PA (US); Anna C. Maroney, Media, PA (US); Jan L. Sechler, Doylestown, PA (US); Richard W. Connors, Harleysville, PA (US); Richard S. Alexander, Newark, DE (US); Maxwell D. Cummings, Wayne, PA (US); Robert A. Galemmo, Paoli, PA (US); Thomas P. Markotan, Morgantown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 90 days.

(21) Appl. No.: 11/377,077

(22) Filed: Mar. 16, 2006

(65) Prior Publication Data

US 2007/0066610 A1    Mar. 22, 2007

Related U.S. Application Data

(60) Provisional application No. 60/689,917, filed on Jun. 13, 2005, provisional application No. 60/663,282, filed on Mar. 18, 2005.

(51) Int. Cl.
| | | |
|---|---|---|
| A61K 31/496 | (2006.01) | |
| A61K 31/404 | (2006.01) | |
| C07D 405/14 | (2006.01) | |
| C07D 405/12 | (2006.01) | |
| C07D 407/14 | (2006.01) | |

(52) U.S. Cl. .................. 514/254.09; 514/414; 514/418; 514/422; 514/323; 514/469; 514/416; 544/373; 544/144; 546/201; 548/454; 548/483; 548/518; 548/525; 548/490; 549/462

(58) Field of Classification Search ................. 514/414, 514/418, 352.2, 323, 422, 254.09, 469; 544/144, 544/373; 546/201; 548/454, 483, 518, 525; 549/462
See application file for complete search history.

(56) References Cited

FOREIGN PATENT DOCUMENTS

| CA | 2352194 | 4/2001 |
|---|---|---|
| DE | 19829229 | 1/1999 |
| DE | 19946289 | 3/2001 |
| DE | 10117823 | 10/2002 |
| EP | 672659 | 1/1999 |
| EP | 694808 | 12/2001 |
| EP | 1193248 | 4/2002 |
| EP | 1229034 | 4/2005 |
| JP | 11007093 | 1/1999 |
| JP | 11015090 | 1/1999 |
| JP | 11302173 | 11/1999 |
| WO | 9901434 | 1/1999 |
| WO | 99/15500 | 4/1999 |
| WO | 9951579 | 10/1999 |
| WO | 200006566 | 2/2000 |
| WO | 200071509 | 11/2000 |
| WO | 200071511 | 11/2000 |
| WO | 2000071493 | 11/2000 |
| WO | 2001023386 | 4/2001 |
| WO | 2002000661 | 1/2002 |
| WO | 2002028823 | 4/2002 |
| WO | 2002040507 | 5/2002 |
| WO | 2002083630 | 10/2002 |
| WO | 2002085888 | 10/2002 |
| WO | 2002096361 | 12/2002 |
| WO | 2002096426 | 12/2002 |
| WO | 2003037328 | 5/2003 |
| WO | 2003097649 | 11/2003 |
| WO | 2004050619 | 6/2004 |
| WO | 2004056178 | 7/2004 |
| WO | 2005005378 | 1/2005 |

OTHER PUBLICATIONS

Wikipedia, definition of "Medicine".*
STN search result STN-11377077A-clear art.*
Fahmy et al. Egyptian Journal of Chemistry, (2003), 46(2), 313-327.*
Bieche, et al., *Int. J. Cancer* 82 (1999), pp. 908-910.
Camp et al., *Cancer* 86 (1999), pp. 2259-2265.
DiRenzo et al., *J. Endocrinol. Invest* 18 (1995), pp. 134-139.
DiRenzo et al., *Oncogene* 19 (2000), pp. 1547-1555.
DiRenzo et al., *Int. J. Cancer* 58(1994), pp. 658-662.

(Continued)

*Primary Examiner*—Yong Chu

(57) ABSTRACT

The invention is directed to acylhydrazones compounds of Formula I:

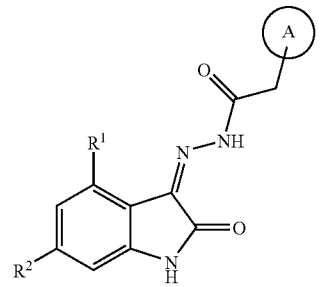

where $R^1$, $R^2$ and A are as defined herein, the use of such compounds as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met. The present invention is further directed to pharmaceutical compositions comprising the compounds of the present invention and to methods for treating conditions such as cancers and other cell proliferative disorders.

12 Claims, 2 Drawing Sheets

OTHER PUBLICATIONS

Dunn et al., Journal of Medicinal Chemistry, 1986, 29 (11), 2326-2329.
Ebert et al., *Cancer Res.* 54 (1994), pp. 5775-5778.
Fischer et al., *Oncogene.* 17 (1998), pp. 733-739.
Ferracini et al., *Oncogene* 10 (1995), pp. 739-749.
Gohji et al., *J. Clin. Oncol.* 18 (2000), pp. 2963-2971.
Hansel et al., *Cancer Res.* 2004 Sep 15;10(18 Pt 1):6152-8.
He et al., Sichuan Da Xue Xue Bao Yi Xue Ban. Jan. 2003 ;34(1):78-9, 88 (*English Abstract Only*; please advise Applicant if the Examiner would like Applicant to submit a complete translation).
Helvitica Chemica Acta, 1928,11, 609-656 (please advise Applicant if the Examiner would like Applicant to submit a complete translation).
Herrera et al., Neoplasia. Jan. 2005;7(1):75-84.
Hjertner et al., *Blood* 94 (1999), pp. 3883-3888.
Humphrey at al., *Am J. Pathol.* 147 (1995), pp. 386-396.
Ichimura et al., *Jpn. J. Cancer Res.* 87 (1996), pp. 1063-1069.
Jucker et al., *Leuk. Res.* 18 (1994), pp. 7-16.
Juillerat et al., Helvitica Chemica Acta, 1976, 59 (3), 855-866.
Kawano et al., Br J Haematol. Nov. 2004;127 3 :305-7.
Klominek et al., *Int. J. Cancer* 76 (1998), pp. 240-249.
Knudsen et al., Adv Cancer Res. 2004;91:31-67.
Kraynack et al., Tetrahedron Letters, 1987, 28 35 , 4027-30.
Kuniyasu et al., *Biochem. Biophys. Res. Commun.* 189 (1992) , pp. 227-232.
Kuniyasu et al., *Int. J. Cancer* 55 (1993), pp. 72-75.
Lee et al., *Oncogene* 19 (2000), pp. 4947-4953.
Lens el et al., *Int J Cancer.* 2005 Feb 10;113 4:678-82.
Liu et al., Am. *J. Pathol.* 142 (1993) , pp. 1155-1162.
Liu et al., *Oncogene.* 7(1992), pp. 181-185.
Marfat et al., Tetrahedron Letters, 1998,39 (42), 7679-7682.
Masuya et al., British Journal of Cancer. 2004; 90:1552-1562.
Maulik et al., *Cytokine Growth Factor Rev.* 2002 Feb;13(1):41-59.
Mederski et al., Bioorganic and Medicinal Chemistry Letters, 1998,8 (1), 17-22.
Meyer et al., Journal of Medicinal Chemistry , 1997, 40(7), 1049-1062.
Michieli et al., Cancer Cell. 2004 Jul.;6(1):61-73.
Millet et al., Bioorganic and Medicinal Chemistry Letters 2002, 12 (24) 3601-3604.
Moon et al., *Mod. Pathol.* 13 (2000), pp. 973-977.
Moriyama et al., *FEBS Lett.* 372 (1995), pp. 78-82.
Nakopoulou et al., *Histopathology* 36 (2000), pp. 313-325.
Nateli et al., *J. Cancer* 68 (1993), pp. 746-750.
Oda et al., *Hum. Pathol.* 31 (2000), pp. 185-192.
Olivero et al., *Br J. Cancer* 74 (1996), pp. 1862-1868.
Olivero et al., *J. Cancer* 82 (1999), pp. 640-643.
Park et al., Cancer Res. 59 (1999), pp. 307-310.
Park et al., 1987, Proc Natl Acad Sci U S A. 84(18):6379-83.
Park et al., Apmis 108 (2000), pp. 195-200.
Parrick et al., Tetrahedron Letters, 2003, 44 (35), 6745-6747.
Pisters et al., *J. Urol.* 154 (1995), pp. 293-298.
Plimmer et al., Journal of Agricultural and Food Chemistry, 1969, 17, 83-85.
Poissonnet, G., Synthetic Communications, 1997, 27 (22), 3839-3846.
Ragan et al., Synthesis, 1998, 11, 1599-1603.
Rygaard et al., *Br J. Cancer* 67 (1993), pp. 37-46.
Sazuki et al., *Hepatology* 20 (1994), pp. 1231-1236.
Schiemann et al., Organic Syntheses, 13, 525, 1933.
Schmidt et al., *Cancer Res.* 58 (1998), pp. 1719-1722.
Schmidt et al., *Oncogene* 18(1999), pp. 2343-2350.
Searcey et al., Tetrahedron Letters, 1984, 25 (29), 3099-3100.
Settimo et al., European Journal of Medicinal Chemistry 1983, 18(3), 261-267.
Shiebley et al., Journal of Organic Chemistry, 1956, 21, 171-173.
Siegfried et al., *Ann Thorac. Surg.* 66 (1998), pp. 1915-1918.
Somei et al., Chemical and Pharmaceutical Bulletin 1981, 29(11), 3145.
Sowter et al., *Int. J. Cancer* 83 (1999), pp. 476-480.
Sun et al., Bioorganic and Medicinal Chemistry Letters, 2004, 14(14), 3799-3802.
Takanami et al., *Oncology* 53 (1996), pp. 392-397.
Thirkettle et al., *Histopathology* 36 (2000), pp. 522-528.
Tokunou et al., *Am J. Pathol.* 158 (2001), pp. 1451-1463.
Tolnay et al., *J. Cancer Res. Clin. Oncol.* 124 (1998), pp. 291-296.
Tsukinoki et al., Oncol Rep. 2004 Nov.;12(5):1017-21.
Umeki et al., *Oncology* 56 (1999), pp. 314-321.
Vinot, Bulletin de la Societe Chimique de France, 1964, 2, 245-247 (please advise Applicant if the Examiner would like Applicant to submit a complete translation).
Wang et al., Organic Letters, 2002, 4(16), 2675-2678.
Zhuang et al., *Nat Genet* 20 (1998), pp. 66-69.
Zeng et al., Clin Exp Metastasis. 2004;21(5):409-17.
International Search Report re: PCT/US2006/009425 dated Jul. 31, 2006.

\* cited by examiner

US 7,662,824 B2

ACYLHYDRAZONES AS KINASE MODULATORS

CROSS REFERENCE TO RELATED APPLICATIONS

This application claims priority to U.S. Provisional Application for Patent No. 60/663,282, filed Mar. 18, 2005, and U.S. Provisional Application for Patent No. 60/689,917 filed Jun. 13, 2005, the entire disclosure of which are hereby incorporated in their entirely.

FIELD OF THE INVENTION

The invention relates to novel compounds that function as protein tyrosine kinase modulators. More particularly, the invention relates to novel compounds that function as inhibitors of c-Met.

BACKGROUND OF THE INVENTION

The present invention relates to acylhydrazones as inhibitors of tyrosine kinases, including c-Met. Acylhydrazones known in the art, including those with therapeutic properties, include: CHEMCATS Accession No. 2004:3793350 Ambinter Stock Screening Collection. (1 Jan. 2004); WO 2003037328 (oxindole hydrazide modulators of protein tyrosine phosphatases); WO 2005005378 (indolinone hydrazides as C-Met inhibitors); WO 2004056178 (pesticidal chloropyridinamino derivatives); US 2004067996 (hydantoins as inhibitors of matrix metalloproteinases and/or TNF-α converting enzyme (TACE)); WO 2003097649 (1-oxa-dibenzoazulenes as inhibitors of tumor necrosis factor production and intermediates for the preparation thereof); WO 2003037328 (oxindole hydrazide modulators of protein tyrosine phosphatases (PTPs)); WO 2002096426 (spiro-fused hydantoin derivatives as inhibitors of matrix metalloproteinases); DE 10117823 and WO 2002083630 (ethanediamides as inhibitors of blood coagulation factor Xa for the treatment of thromboembolic illnesses); WO 2002040507 (novel compounds for use in radioimmunoscintigraphy and/or radioimmunotherapy of cancers); EP 1193248 and WO 2002028823 (arylmalonamides and -malonamic esters with as Factor VIIa inhibitors with antithrombotic activity); WO 2002000661 (pyrrolo[2,3-d]pyrimidines as immunosuppressive agents); DE 19946289 and WO 2001023386 (2-phenyl-5,6-dihydro-imidazo[4,5,1-jk][1,4]benzodiazepin-7(4H)-ones as poly(ADP ribose) polymerase inhibitors); WO 2000071511 (benzamidines as inhibitors of factor Xa); WO 2000071493 (benzamidines and arylamidines as inhibitors of factor Xa); WO 2000071509 (benzamidines and arylamidines as inhibitors of factor Xa); U.S. Pat. No. 6,075,044 (Isobenzofurandione and hydrazonodihydroindolone derivatives as protozoacides, acting as inhibitors of purine salvage phosphoribosyltransferases); JP 11302173 (Benzamide derivatives as histone deacetylase inhibitors for treating tumors and other diseases); WO 9951579 ([[[(alkoximino) alkoxy]methyl]phenyl]aloximinoacetates and analogs as agrochemical fungicides); JP 11015090 (silver halide photographic material for printing platemaking); JP 11007093 (photographic emulsion containing high-sensitive oxalylhydrazine derivative for graphic arts); WO 9901434 (imidazole-containing quinoline and benzazepine derivatives as inhibitors of farnesyl protein transferase); DE 19829229 and U.S. Pat. No. 6,235,787 (hydroxycarbamoylalkylcarboxylic acid hydrazides as inhibitors of tumor necrosis factor and transforming growth factor release); WO 9825901 (spiro[indoli- none] derivatives as vasopressin V2 receptor antagonists); WO 9739748 (acrylic acids as modulators of molecules with phosphotyrosine recognition units); WO 9731910 (heterocyclic fibrinogen receptor antagonists); WO 9729073 (substituted amide derivatives as protein-farnesyl transferase inhibitors); U.S. Pat. No. 5,550,003 (silver halide photographic photosensitive material); EP 694808 (Process of forming super high-contrast negative images and silver halide photographic material and developer being used therefore); and EP 672659 (L-Arginine aldehyde peptide derivatives useful as antithrombotic agents).

Protein kinases are enzymatic components of the signal transduction pathways which catalyze the transfer of the terminal phosphate from ATP to the hydroxy group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefits of kinase inhibition has also been studied. In sum, inhibitors of protein kinases have particular utility in the treatment of human and animal disease.

The hepatocyte growth factor (HGF) (also known as scatter factor) receptor, c-Met, is a receptor tyrosine kinase which regulates cell proliferation, morphogenesis, and motility. The c-Met gene is translated into a 170 kD protein which is processed into a cell surface receptor composed of a 140 kD β transmembrane subunit and 50 kD glycosylated extracellular α subunit.

Mutations in c-Met, over-expression of c-Met and/or HGF/SF, expression of c-Met and HGF/SF by the same cell, and overexpression and/or aberrant c-Met signaling is present in a variety of human solid tumors and is believed to participate in angiogenesis, tumor development, invasion, and metastasis.

Cell lines with uncontrolled c-Met activation, for example, are both highly invasive and metastatic. A notable difference between normal and transformed cells expressing c-Met receptor is that phosphorylation of the tyrosine kinase domain in tumor cells is often independent of the presence of ligand.

C-Met mutations/alterations have been identified in a number of human diseases, including tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—and leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma).

See Maulik G, Shrikhande A, Kijima T, Ma P C, Morrison P T, Salgia R., Role of the hepatocyte growth factor receptor, c-Met, in oncogenesis and potential for therapeutic inhibition. *Cytokine Growth Factor Rev.* 2002 February; 13(1):41-59, and cites therein: Bieche, M. H. Champeme and R. Lidereau, Infrequent mutations of the MET gene in sporadic breast tumours (letter). *Int. J. Cancer* 82 (1999), pp. 908-910; R. L. Camp, E. B. Rimm and D. L. Rimm, Met expression is associated with poor outcome in patients with axillary lymph node negative breast carcinoma. *Cancer* 86 (1999), pp. 2259-2265; L. Nakopoulou, H. Gakiopoulou, A. Keramopoulos et al., c-met tyrosine kinase receptor expression is associated with abnormal beta-catenin expression and favourable prognostic factors in invasive breast carcinoma. *Histopathology* 36 (2000), pp. 313-325; C. Liu, M. Park and M. S. Tsao, Over-expression of c-met proto-oncogene but not epidermal growth factor receptor or c-erbB-2 in primary human colorectal carcinomas. *Oncogene.* 7 (1992), pp. 181-185; K. Umeki, G. Shiota and H. Kawasaki, Clinical significance of c-met oncogene alterations in human colorectal cancer. *Oncology* 56 (1999), pp. 314-321; H. Kuniyasu, W. Yasui, Y. Kitadai et al., Frequent amplification of the c-met gene in scirrhous type stomach cancer. *Biochem. Biophys. Res. Commun.* 189 (1992), pp. 227-232; H. Kuniyasu, W. Yasui, H. Yokozaki et al., Aberrant expression of c-met mRNA in human gastric carcinomas. *Int. J. Cancer* 55 (1993), pp. 72-75; W. S. Park, R. R. Oh, Y. S. Kim et al., Absence of mutations in the kinase domain of the Met gene and frequent expression of Met and HGF/SF protein in primary gastric carcinomas. Apmis 108 (2000), pp. 195-200; J. H. Lee, S. U. Han, H. Cho et al., A novel germ line juxtamembrane Met mutation in human gastric cancer. *Oncogene* 19 (2000), pp. 4947-4953; T. Moriyama, H. Kataoka, H. Tsubouchi et al., Concomitant expression of hepatocyte growth factor (HGF), HGF activator and c-met genes in human glioma cells in vitro. *FEBS Lett.* 372 (1995), pp. 78-82; Y. W. Moon, R. J. Weil, S. D. Pack et al., Missense mutation of the MET gene detected in human glioma. *Mod. Pathol.* 13 (2000), pp. 973-977; M. Di Renzo, M. Olivero, T. Martone et al., Somatic mutations of the met oncogene are selected during metastatic spread of human HNSC carcinomas. *Oncogene* 19 (2000), pp. 1547-1555; K. Suzuki, N. Hayashi, Y. Yamada et al., Expression of the c-met proto-oncogene in human hepatocellular carcinoma. *Hepatology* 20 (1994), pp. 1231-1236; W. S. Park, S. M. Dong, S. Y. Kim et al., Somatic mutations in the kinase domain of the Met/hepatocyte growth factor receptor gene in childhood hepatocellular carcinomas. Cancer Res. 59 (1999), pp. 307-310; L. Schmidt, K. Junker, G. Weirich et al., Two North American families with hereditary papillary renal carcinoma and identical novel mutations in the MET proto-oncogene. *Cancer Res.* 58 (1998), pp. 1719-1722; J. Fischer, G. Palmedo, R. von Knobloch et al., Duplication and over-expression of the mutant allele of the MET proto-oncogene in multiple hereditary papillary renal cell tumours. *Oncogene.* 17 (1998), pp. 733-739; Z. Zhuang, W. S. Park, S. Pack et al., Trisomy 7-harbouring non-random duplication of the mutant MET allele in hereditary papillary renal carcinomas. *Nat Genet* 20 (1998), pp. 66-69; M. Olivero, G. Valente, A. Bardelli et al., Novel mutation in the ATP-binding site of the MET oncogene tyrosine kinase in a HPRCC family. *Int. J. Cancer* 82 (1999), pp. 640-643; L. Schmidt, K. Junker, N. Nakaigawa et al., Novel mutations of the MET proto-oncogene in papillary renal carcinomas. *Oncogene* 18 (1999), pp. 2343-2350; M. Jucker, A. Gunther, G. Gradl et al., The Met/hepatocyte growth factor receptor (HGFR) gene is over-expressed in some cases of human leukemia and lymphoma. *Leuk. Res.* 18 (1994), pp. 7-16; E. Tolnay, C. Kuhnen, T. Wiethege et al., Hepatocyte growth factor/scatter factor and its receptor c-Met are over-expressed and associated with an increased microvessel density in malignant pleural mesothelioma. *J. Cancer Res. Clin. Oncol.* 124 (1998), pp. 291-296; J. Klominek, B. Baskin, Z. Liu et al., Hepatocyte growth factor/scatter factor stimulates chemotaxis and growth of malignant mesothelioma cells through c-met receptor. *Int. J. Cancer* 76 (1998), pp. 240-249; Thirkettle, P. Harvey, P. S. Hasleton et al., Immunoreactivity for cadherins, HGF/SF, met, and erbB-2 in pleural malignant mesotheliomas. *Histopathology* 36 (2000), pp. 522-528; P. G. Natali, M. R. Nicotra, M. F. Di Renzo et al., Expression of the c-Met/HGF receptor in human melanocytic neoplasms: demonstration of the relationship to malignant melanoma tumour progression. *Br. J. Cancer.* 68 (1993), pp. 746-750; O. Hjertner, M. L. Torgersen, C. Seidel et al., Hepatocyte growth factor (HGF) induces interleukin-11 secretion from osteoblasts: a possible role for HGF in myeloma-associated osteolytic bone disease. *Blood* 94 (1999), pp. 3883-3888; C. Liu and M. S. Tsao, In vitro and in vivo expressions of transforming growth factor-alpha and tyrosine kinase receptors in human non-small-cell lung carcinomas. *Am. J. Pathol.* 142 (1993), pp. 1155-1162; M. Olivero, M. Rizzo, R. Madeddu et al., Over-expression and activation of hepatocyte growth factor/scatter factor in human non-small-cell lung carcinomas. *Br J. Cancer* 74 (1996), pp. 1862-1868; E. Ichimura, A. Maeshima, T. Nakajima et al., Expression of c-met/HGF receptor in human non-small cell lung carcinomas in vitro and in vivo and its prognostic significance. *Jpn. J. Cancer Res.* 87 (1996), pp. 1063-1069; Takanami, F. Tanana, T. Hashizume et al., Hepatocyte growth factor and c-Met/hepatocyte growth factor receptor in pulmonary adenocarcinomas: an evaluation of their expression as prognostic markers. *Oncology* 53 (1996), pp. 392-397; J. M. Siegfried, L. A. Weissfeld, J. D. Luketich et al., The clinical significance of hepatocyte growth factor for non-small cell lung cancer. *Ann Thorac. Surg.* 66 (1998), pp. 1915-1918; M. Tokunou, T. Niki, K. Eguchi et al., c-MET expression in myofibroblasts: role in autocrine activation and prognostic significance in lung adenocarcinoma. *Am J. Pathol.* 158 (2001), pp. 1451-1463; R. Ferracini, M. F. Di Renzo, K. Scotlandi et al., The Met/HGF receptor is over-expressed in human osteosarcomas and is activated by either a paracrine or an autocrine circuit. *Oncogene* 10 (1995), pp. 739-749; M. F. Di Renzo, M. Olivero, D. Katsaros et al., Over-expression of the Met/HGF receptor in ovarian cancer. *Int. J. Cancer* 58(1994), pp. 658-662; H. M. Sowter, A. N. Corps and S. K. Smith, Hepatocyte growth factor (HGF) in ovarian epithelial tumour fluids stimulates the migration of ovarian carcinoma cells. *Int. J. Cancer* 83 (1999), pp. 476-480; M. Ebert, M. Yokoyama, H. Friess et al., Co-expression of the c-met proto-oncogene and hepatocyte growth factor in human pancreatic cancer. *Cancer Res.* 54 (1994), pp. 5775-5778; L. L. Pisters, P. Troncoso, H. E. Zhau et al., c-met proto-oncogene expression in benign and malignant human prostate tissues. *J. Urol.* 154 (1995), pp. 293-298; P. A. Humphrey, X. Zhu, R. Zarnegar et al., Hepatocyte growth factor and its receptor (c-MET) in prostatic carcinoma. *Am J. Pathol.* 147 (1995), pp. 386-396; K. Rygaard, T. Nakamura, M. Spang-Thomsen et al., Expression of the proto-oncogenes c-met and c-kit and their ligands, hepatocyte growth factor/scatter factor and stem cell factor, in SCLC cell lines and xenografts. *Br J. Cancer* 67 (1993), pp. 37-46; Y. Oda, A. Sakamoto, T. Saito et al., Expression of hepatocyte growth factor (HGF)/scatter factor and its receptor c-MET correlates with poor prognosis in synovial sarcoma. *Hum. Pathol.* 31 (2000), pp. 185-192; M. F.

Di Renzo, M. Olivero, G. Serini et al., Over-expression of the c-MET/HGF receptor in human thyroid carcinomas derived from the follicular epithelium. *J. Endocrinol. Invest* 18 (1995), pp. 134-139; K. Gohji, M. Nomi, Y. Niitani et al., Independent prognostic value of serum hepatocyte growth factor in bladder cancer. *J. Clin. Oncol.* 18 (2000), pp. 2963-2971.

Because of the role of aberrant HGF/SF-Met signaling in the pathogenesis of various human cancers, inhibitors of c-Met receptor tyrosine kinase have broad applications in the treatment of cancers in which Met activity contributes to the invasive/metastatic phenotype, including those in which c-Met is not overexpressed or otherwise altered. Inhibitors of c-Met also inhibit angiogenesis and therefore are believed to have utility in the treatment of diseases associated with the formation of new vasculature, such as rheumatoid, arthritis, retinopathy. See, Michieli P, Mazzone M, Basilico C, Cavassa S, Sottile A, Naldini L, Comoglio P M. Targeting the tumor and its microenvironment by a dual-function decoy Met receptor. Cancer Cell. 2004 July; 6(1):61-73.

Over-expression of c-Met is also believed to be a potentially useful predictor for the prognosis of certain diseases, such as, for example, breast cancer, non-small cell lung carcinoma, pancreatic endocrine neoplasms, prostate cancer, esophageal adenocarcinoma, colorectal cancer, salivary gland carcinoma, diffuse large B-cell lymphoma and endometrial carcinoma.

See Herrera L J, El-Hefnawy T, Queiroz de Oliveira P E, Raja S, Finkelstein S, Gooding W, Luketich J D, Godfrey T E, Hughes S J., The HGF Receptor c-Met Is Overexpressed in Esophageal Adenocarcinoma. *Neoplasia*. 2005 January; 7(1):75-84; Zeng Z, Weiser M R, D'Alessio M, Grace A, Shia J, Paty P B., Immunoblot analysis of c-Met expression in human colorectal cancer: overexpression is associated with advanced stage cancer. *Clin Exp Metastasis*. 2004; 21(5): 409-17; He Y, Peng Z, Pan X, Wang H, Ouyang Y. [Expression and correlation of c-Met and estrogen receptor in endometrial carcinomas] *Sichuan Da Xue Xue Bao Yi Xue Ban*. 2003 January; 34(1):78-9, 88 (English Abstract Only); Tsukinoki K, Yasuda M, Mori Y, Asano S, Naito H, Ota Y, Osamura R Y, Watanabe Y. Hepatocyte growth factor and c-Met immunoreactivity are associated with metastasis in high grade salivary gland carcinoma. *Oncol Rep*. 2004 November; 12(5):1017-21; Kawano R, Ohshima K, Karube K, Yamaguchi T, Kohno S, Suzumiya J, Kikuchi M, Tamura K. Prognostic significance of hepatocyte growth factor and c-MET expression in patients with diffuse large B-cell lymphoma. Br *J Haematol*. 2004 November; 127(3):305-7; Lengyel E, Prechtel D, Resau J H, Gauger K, Welk A, Lindemann K, Salanti G, Richter T, Knudsen B, Vande Woude G F, Harbeck N. C-Met overexpression in node-positive breast cancer identifies patients with poor clinical outcome independent of Her2/neu. *Int J Cancer*. 2005 Feb. 10; 113(4):678-82; Hansel D E, Rahman A, House M, Ashfaq R, Berg K, Yeo C J, Maitra A. Met proto-oncogene and insulin-like growth factor binding protein 3 overexpression correlates with metastatic ability in well-differentiated pancreatic endocrine neoplasms. *Clin Cancer Res*. 2004 Sep. 15; 10(18 Pt 1):6152-8; Knudsen B S, Edlund M. Prostate cancer and the met hepatocyte growth factor receptor. *Adv Cancer Res*. 2004; 91:31-67; D Masuya, C Huang, D Liu, T Nakashima, et al., The tumour-stromal interaction between intratumoral c-Met and stromal hepatocyte growth factor associated with tumour growth and prognosis in non-small-cell lung cancer patients. *British Journal of Cancer*. 2004; 90:1552-1562; Ernst Lengyel, Dieter Prechtel, James H. Resau, Katja Gauger, et al. C-Met overexpression in node-positive breast cancer identifies patients with poor clinical outcome independent of Her2/neu. Int. J. Cancer 2005; 113: 678-682.

SUMMARY OF THE INVENTION

The present invention provides novel acylhydrazones (the compounds of Formula I) as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met.

Illustrative of the invention is a pharmaceutical composition comprising a compound of Formula I and a pharmaceutically acceptable carrier. Another illustration of the present invention is a pharmaceutical composition prepared by mixing any of the compounds of Formula I and a pharmaceutically acceptable carrier.

Other features and advantages of the invention will be apparent from the following detailed description of the invention and from the claims.

DETAILED DESCRIPTION OF THE INVENTION

Definitions

Figure 1:
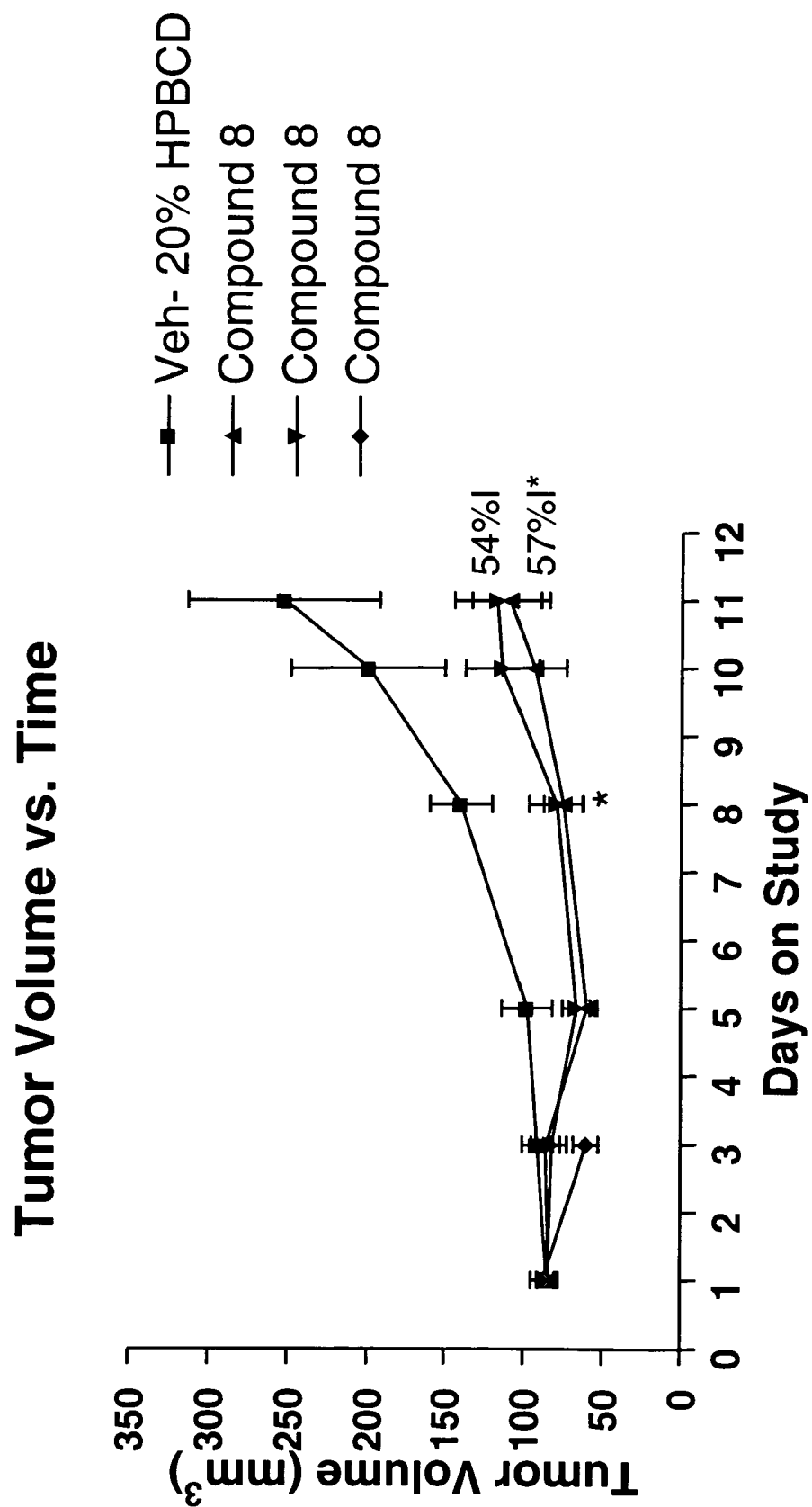
FIG. 1 shows the time course of the inhibitory effects of compounds of the present invention on the growth of U87MG tumor xenografts in nude mice.

As used herein, the following terms are intended to have the following meanings (additional definitions are provided where needed throughout the Specification):

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl," whether used alone or as part of a substituent group, refers to a saturated branched or straight chain monovalent hydrocarbon radical, wherein the radical is derived by the removal of one hydrogen atom from a single carbon atom. Unless specifically indicated (e.g. by the use of a limiting term such as "terminal carbon atom"), substituent variables may be placed on any carbon chain atom. Typical alkyl radicals include, but are not limited to, methyl, ethyl, propyl, isopropyl and the like. Examples include $C_{1-8}$alkyl, $C_{1-6}$alkyl and $C_{1-4}$alkyl groups.

The term "alkylamino" refers to a radical formed by the removal of one hydrogen atom from the nitrogen of an alkylamine, such as butylamine, and the term "dialkylamino" refers to a radical formed by the removal of one hydrogen atom from the nitrogen of a secondary amine, such as dibutylamine. In both cases it is expected that the point of attachment to the rest of the molecule is the nitrogen atom.

The term "alkynyl," whether used alone or as part of a substituent group, refers to a partially unsaturated branched or straight chain monovalent hydrocarbon radical having at least one carbon-carbon triple bond, whereby the triple bond is derived by the removal of two hydrogen atoms from each of two adjacent carbon atoms of a parent alkyl molecule and the radical is derived by the removal of one hydrogen atom from a single carbon atom. Typical alkynyl radicals include ethynyl, propynyl, butynyl and the like. Examples include $C_{2-8}$alkynyl or $C_{2-4}$alkynyl groups.

The term "alkoxy" refers to a saturated or partially unsaturated branched or straight chain monovalent hydrocarbon alcohol radical derived by the removal of the hydrogen atom from the hydroxide oxygen substituent on a parent alkane, alkene or alkyne. Where specific levels of saturation are intended, the nomenclature "alkoxy", "alkenyloxy" and "alkynyloxy" are used consistent with the definitions of alkyl, alkenyl and alkynyl. Examples include $C_{1-8}$alkoxy or $C_{1-4}$alkoxy groups.

The term "alkoxyether" refers to a saturated branched or straight chain monovalent hydrocarbon alcohol radical derived by the removal of the hydrogen atom from the hydroxide oxygen substituent on a hydroxyether. Examples include 1-hydroxyl-2-methoxy-ethane or 1-(2-hydroxylethoxy)-2-methoxy-ethane groups.

The term "aralkyl" refers to a $C_{1-6}$ alkyl group containing an aryl substituent. Examples include benzyl, phenylethyl or 2-naphthylmethyl. It is intended that the point of attachment to the rest of the molecule be the alkyl group.

The term "aromatic" refers to a cyclic hydrocarbon ring system having an unsaturated, conjugated π electron system.

The term "aryl" refers to an aromatic cyclic hydrocarbon ring radical derived by the removal of one hydrogen atom from a single carbon atom of the ring system. Typical aryl radicals include phenyl, naphthalenyl, fluorenyl, indenyl, azulenyl, anthracenyl and the like.

The term "arylamino" refers to an amino group, such as ammonia, substituted with an aryl group, such as phenyl. It is expected that the point of attachment to the rest of the molecule is through the nitrogen atom.

The term "benzo-fused cycloalkyl" refers to a bicyclic fused ring system radical wherein one of the rings is benzene and the other is a cycloalkyl or cycloalkenyl ring. Typical benzo-fused cycloalkyl radicals include indanyl, 1,2,3,4-tetrahydro-naphthalenyl, 6,7,8,9,-tetrahydro-5H-benzocycloheptenyl, 5,6,7,8,9,10-hexahydro-benzocyclooctenyl and the like. A benzo-fused cycloalkyl ring system is a subset of the aryl group.

The term "benzo-fused heteroaryl" refers to a bicyclic fused ring system radical wherein one of the rings is benzene and the other is a heteroaryl ring. Typical benzo-fused heteroaryl radicals include indolyl, indolinyl, isoindolyl, benzo[b]furyl, benzo[b]thienyl, indazolyl, benzthiazolyl, quinolinyl, isoquinolinyl, cinnolinyl, phthalazinyl, quinazolinyl, and the like. A benzo-fused heteroaryl ring is a subset of the heteroaryl group.

The term "benzo-fused heterocyclyl" refers to a bicyclic fused ring system radical wherein one of the rings is benzene and the other is a heterocyclyl ring. Typical benzo-fused heterocyclyl radicals include 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl and the like.

The term "carboxyalkyl" refers to an alkylated carboxy group such as tert-butoxycarbonyl, in which the point of attachment to the rest of the molecule is the carbonyl group.

The term "cyclic heterodionyl" refers to a heterocyclic compound bearing two carbonyl substituents. Examples include thiazolidine diones, oxazolidine diones and pyrrolidine diones.

The term "cycloalkenyl" refers to a partially unsaturated cycloalkyl radical derived by the removal of one hydrogen atom from a hydrocarbon ring system that contains at least one carbon-carbon double bond. Examples include cyclohexenyl, cyclopentenyl and 1,2,5,6-cyclooctadienyl.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{3-8}$cycloalkyl, $C_{5-8}$cycloalkyl, $C_{3-12}$cycloalkyl, $C_{3-20}$cycloalkyl, decahydronaphthalenyl, and 2,3,4,5,6,7-hexahydro-1H-indenyl.

The term "fused ring system" refers to a bicyclic molecule in which two adjacent atoms are present in each of the two cyclic moieties. Heteroatoms may optionally be present. Examples include benzothiazole, 1,3-benzodioxole and decahydronaphthalene.

The term "hetero" used as a prefix for a ring system refers to the replacement of at least one ring carbon atom with one or more atoms independently selected from N, S, O or P. Examples include rings wherein 1, 2, 3 or 4 ring members are a nitrogen atom; or, 0, 1, 2 or 3 ring members are nitrogen atoms and 1 member is an oxygen or sulfur atom.

The term "heteroaralkyl" refers to a $C_{1-6}$ alkyl group containing a heteroaryl substituent. Examples include furylmethyl and pyridylpropyl. It is intended that the point of attachment to the rest of the molecule be the alkyl group.

The term "heteroaryl" refers to a radical derived by the removal of one hydrogen atom from a ring carbon atom of a heteroaromatic ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "heteroaryl-fused cycloalkyl" refers to a bicyclic fused ring system radical wherein one of the rings is cycloalkyl and the other is heteroaryl. Typical heteroaryl-fused cycloalkyl radicals include 5,6,7,8-tetrahydro-4H-cyclohepta(b)thienyl, 5,6,7-trihydro-4H-cyclohexa(b)thienyl, 5,6-dihydro-4H-cyclopenta(b)thienyl and the like.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrole, 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "squaryl" refers to a cyclobutyl 1,2 dione radical.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

The term "independently selected" refers to one or more substituents selected from a group of substituents, wherein the substituents may be the same or different.

The substituent nomenclature used in the disclosure of the present invention was derived by first indicating the atom having the point of attachment, followed by the linking group atoms toward the terminal chain atom from left to right, substantially as in:

$(C_{1-6})alkylC(O)NH(C_{1-6})alkyl(Ph)$ or by first indicating the terminal chain atom, followed by the linking group atoms toward the atom having the point of attachment, substantially as in:

$Ph(C_{1-6})alkylamido(C_{1-6})alkyl$ either of which refers to a radical of the Formula:

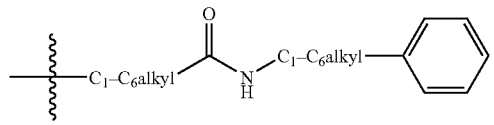

Lines drawn into ring systems from substituents indicate that the bond may be attached to any of the suitable ring atoms.

When any variable (e.g. $R_4$) occurs more than one time in any embodiment of Formula I, each definition is intended to be independent.

The terms "comprising", "including", and "containing" are used herein in their open, non-limited sense.

Nomenclature

Except where indicated, compound names were derived using nomenclature rules well known to those skilled in the art, by either standard IUPAC nomenclature references, such as *Nomenclature of Organic Chemistry, Sections A, B, C, D, E, F and H*, (Pergamon Press, Oxford, 1979, Copyright 1979 IUPAC) and *A Guide to IUPAC Nomenclature of Organic Compounds* (*Recommendations* 1993), (Blackwell Scientific Publications, 1993, Copyright 1993 IUPAC), or commercially available software packages such as Autonom (brand of nomenclature software provided in the ChemDraw Ultra® office suite marketed by CambridgeSoft.com) and ACD/Index Name™ (brand of commercial nomenclature software marketed by Advanced Chemistry Development, Inc., Toronto, Ontario).

Abbreviations

As used herein, the following abbreviations are intended to have the following meanings (additional abbreviations are provided where needed throughout the Specification):

| | |
|---|---|
| Boc | tert-butoxycarbonyl |
| DCM | dichloromethane |
| DMF | dimethylformamide |
| DMSO | dimethylsulfoxide |
| DIEA | diisopropylethylamine |
| EDTA | ethylenediaminetetraaceticacid |
| EDC | 1-(3-dimethylaminopropyl)-3-ethylcarbodiimide hydrochloride |
| EtOAc | ethyl acetate |
| HOBT | 1-hydroxybenzotriazole hydrate |
| HBTU | O-benzotriazol-1-yl-N,N,N',N'-tetramethyluronium hexafluorophosphate |
| i-PrOH | isopropyl alcohol |
| LC/MS (ESI) | Liquid chromatography/mass spectrum (electrospray ionization) |
| MeOH | Methyl alcohol |
| NMM | N-methylmorpholine |
| NMR | nuclear magnetic resonance |
| PS | polystyrene |
| RT | room temperature |
| NaHMDS | sodium hexamethyldisilazane |
| TEA | triethylamine |
| TFA | trifluoroacetic acid |
| THF | tetrahydrofuran |
| TLC | thin layer chromatography |

Formula I

The present invention comprises compounds of Formula I:

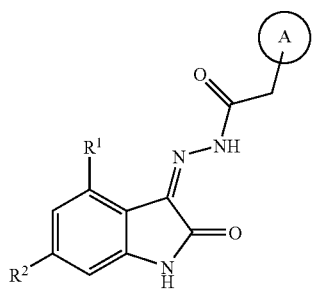

Formula I pharmaceutically acceptable salts, N-oxides, and stereochemical isomers thereof, wherein:

A is a benzo-fused heterocyclic ring or a benzo-fused heteroaryl ring, wherein the point of attachment of said ring is through the benzo moiety; said ring is optionally substituted with —$NH_2$, —$CH_3$, —$CF_3$, —$NO_2$, —CN, Cl, F, Br, or carbonyl;

$R^1$ is hydrogen or halogen;

$R^2$ is selected from the group consisting of Formula II, Formula III or Formula IV;

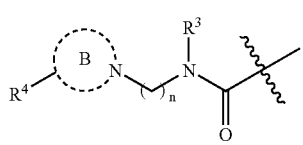

Formula II

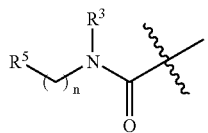

Formula III

-continued

Formula IV wherein n is 2, 3 or 4;
B is a nitrogen containing heterocyclic ring, preferably selected from R³ is hydrogen or alkyl;
R⁴ is H, alkyl, hydroxyalkyl, hydroxyl, or —C(O)alkyl; and
R⁵ is OH, NH-alkyl, N-alkyl₂, or NH₂.

As used hereafter, the terms "compound of Formula I" and "compounds of Formula I" are meant to include also the pharmaceutically acceptable salts, N-oxides and stereochemical isomers thereof.

EMBODIMENTS OF FORMULA I

Preferred embodiments of the invention are compounds of Formula I wherein one or more of the following limitations are present:

R¹ is hydrogen, Cl or Br;

A is selected from:

-continued

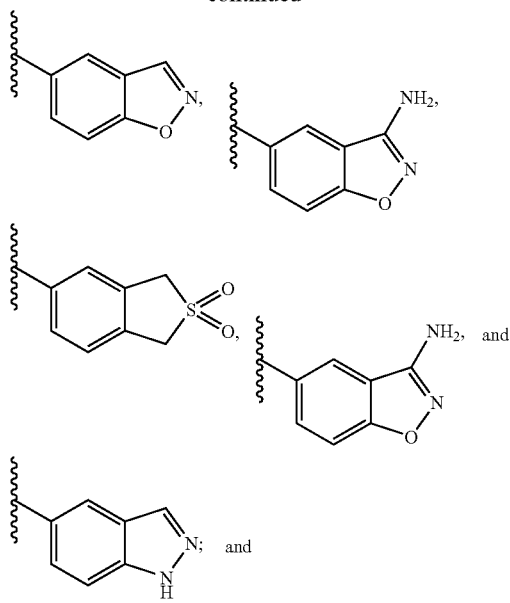

$R^2$ is Formula II wherein:
  n is 2 or 3;
  B is morpholinyl, piperidinyl, piperazinyl, or pyrrolidinyl;
  $R^3$ is hydrogen; and
  $R^4$ is hydrogen, hydroxyl, hydroxymethyl, methyl, ethyl, propyl or isopropyl.

Another preferred embodiment of the invention are compounds of Formula I wherein one or more of the following limitations are present:

$R^1$ is hydrogen, Cl or Br;
A is

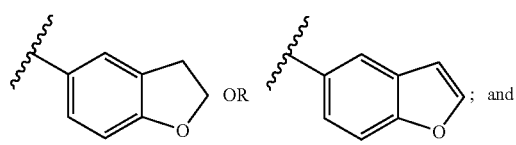

$R^2$ is Formula II wherein:
  n is 2 or 3;
  B is morpholinyl, piperidinyl, piperazinyl, or pyrrolidinyl;
  $R^3$ is hydrogen; and
  $R^4$ is hydrogen, hydroxyl, hydroxymethyl, methyl, ethyl, propyl or isopropyl.

Other preferred embodiments of the invention are compounds of Formula I wherein one or more of the following limitations are present:

$R^1$ is hydrogen, Cl or Br;
A is

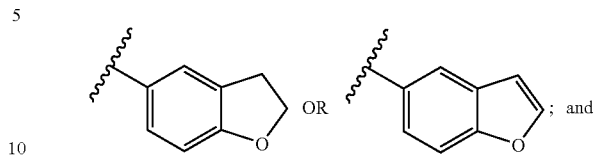

$R^2$ is Formula III wherein:
  n is 2 or 3;
  $R^3$ is hydrogen; and
  $R^5$ is hydroxyl, methylamino, ethylamino, propylamino, isopropylamino, dimethylamino, diethylamino, dipropylamino, methylethylamino, or methylpropylamino.

Other preferred embodiments of the invention are compounds of Formula I wherein one or more of the following limitations are present:

$R^1$ is hydrogen, Cl or Br;
A is

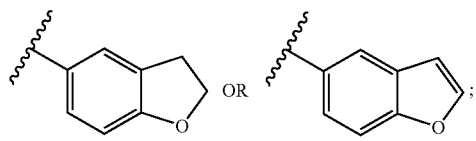

$R^2$ is Formula IV wherein:
  B is morpholinyl, piperidinyl, piperazinyl, or pyrrolidinyl; and
  $R^4$ is hydrogen, hydroxyl, hydroxymethyl, methyl, ethyl, propyl or isopropyl.

Other preferred embodiments of the invention are compounds of Formula I wherein one or more of the following limitations are present:

$R^1$ is hydrogen, Cl or Br;
A is

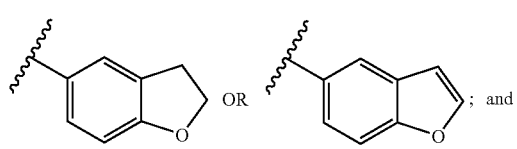

$R^2$ is Formula III wherein:
  n is 2 or 3; and
  $R^3$ is hydrogen; and
  $R^5$ is hydroxyl, dimethylamino, diethylamino, or dipropylamino.

Other embodiments of the invention are compounds of Formula I wherein one or more of the following limitations are present:

$R^1$ is hydrogen, Cl or Br;

A is

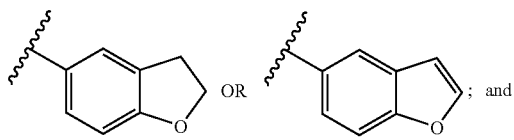

$R^2$ is Formula IV wherein:
 B is piperazine; and
 $R^4$ is hydrogen, methyl, ethyl, propyl or isopropyl.

Pharmaceutically Acceptably Salts

The compounds of the present invention may also be present in the form of pharmaceutically acceptable salts.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

Prodrugs

The present invention includes within its scope prodrugs of the compounds of the invention. In general, such prodrugs will be functional derivatives of the compounds which are readily convertible in vivo into an active compound. Thus, in the methods of treatment of the present invention, the term "administering" shall encompass the means for treating, ameliorating or preventing a syndrome, disorder or disease described herein with a compound specifically disclosed or a compound, or prodrug thereof, which would obviously be included within the scope of the invention albeit not specifically disclosed for certain of the instant compounds. Conventional procedures for the selection and preparation of suitable prodrug derivatives are described in, for example, "Design of Prodrugs", ed. H. Bundgaard, Elsevier, 1985.

Stereochemically Isomeric Forms

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds of Formula I and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are stereoisomers wherein an asymmetrically substituted carbon atom acts as a chiral center.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Polymorphs

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

N-Oxides

The compounds of Formula I may be converted to the corresponding N-oxide forms following art-known procedures for converting a trivalent nitrogen into its N-oxide form. Said N-oxidation reaction may generally be carried out by reacting the starting material of Formula I with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tbutyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Tautomeric Forms

Some of the compounds of Formula I may also exist in their tautomeric forms. Such forms although not explicitly indicated in the present application are intended to be included within the scope of the present invention.

Preparation of Compounds of the Present Invention

During any of the processes for preparation of the compounds of the present invention, it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, 3rd ed. Wiley Interscience, 1999. The protecting groups may be removed at a convenient subsequent stage using methods known in the art.

General Reaction Scheme

Compounds of Formula I can be prepared by methods known to those who are skilled in the art. The following reaction schemes are only meant to represent examples of the invention and are in no way meant to be a limit of the invention.

Aryl and heteroaryl acetic acids can be accessed by methods known in the art (Journal of Medicinal Chemistry, 1986, 29 (11), 2326-2329; Bioorganic and Medicinal Chemistry Letters, 2004, 14(14), 3799-3802; EP 1229034 A1 20020807; Tetrahedron Letters, 2003, 44 (35), 6745-6747; Synthetic Communications, 1997, 27 (22), 3839-3846). Several examples of aryl acetic acid synthesis are illustrated in Scheme 1. Benzofused heterocyclic compound (1-1), (Journal of Medicinal Chemistry, 1996, 29 (11), 2362-2369; Journal of Medicinal Chemistry, 1997, 40(7), 1049-1062), is treated with N-bromosuccinimide in carbon tetrachloride to give compound 1-2. Nitrophenylacetic acid (1-3), (Bioorganic and Medicinal Chemistry Letters, 1998, 8 (1), 17-22; Organic Letters, 2002, 4 (16), 2675-2678; WO 00/06566, Helvitica Chemica Acta, 1976, 59 (3), 855-866) is reduced with conditions such as hydrogenation in the presence of palladium on activated carbon in a solvent such as methanol to give compound 1-4, which is then treated with triethyl orthoformate in toluene to give 1-5. Compound 1-6 can be treated with an appropriate amine to give Compound 1-7. Compound 1-8 can be treated with hydroxylamine hydrochloride in ethanol, followed by a Mitsunobu reaction to give Compound 1-9. This can be treated with sodium hydroxide in methanol to give Compound 1-10.

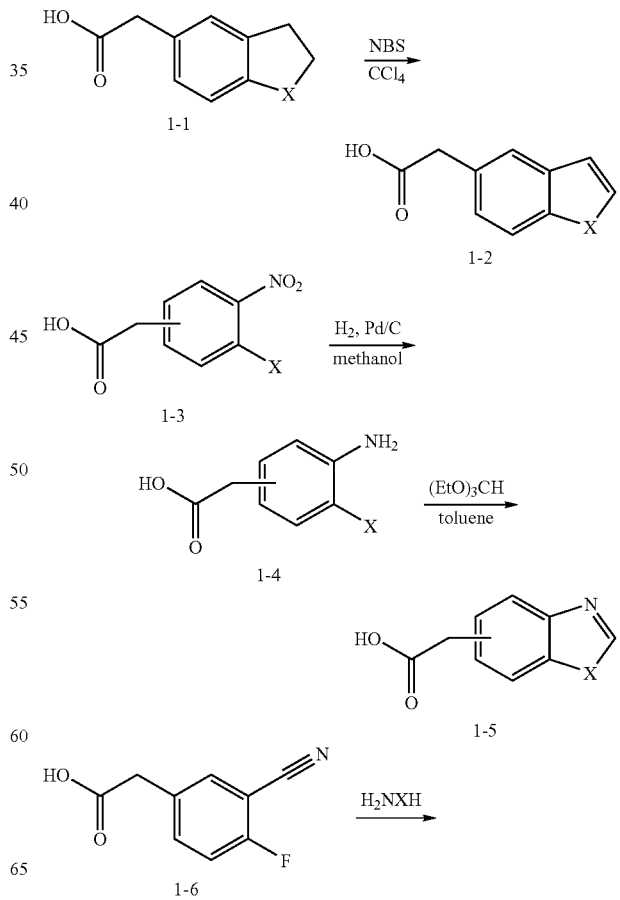

Scheme 1

-continued

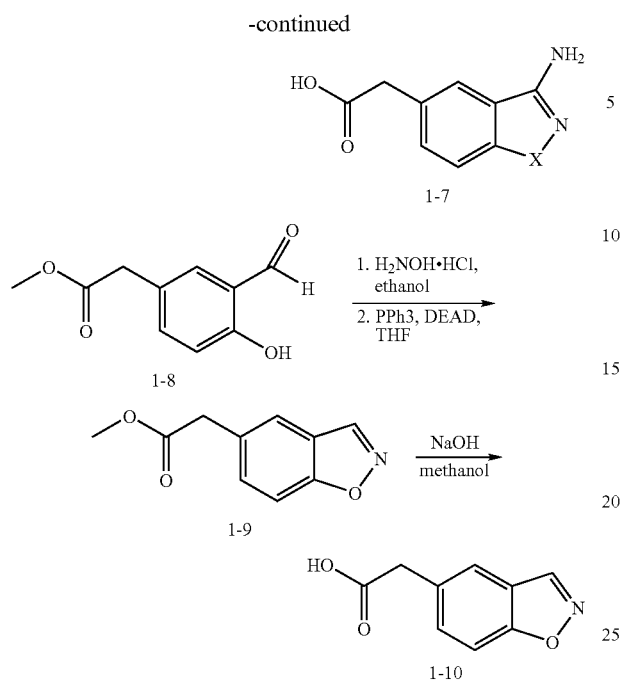

wherein X is NH, O or S.

The following compounds can be synthesized by methods known in the art:

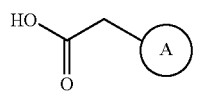

where A is selected from:

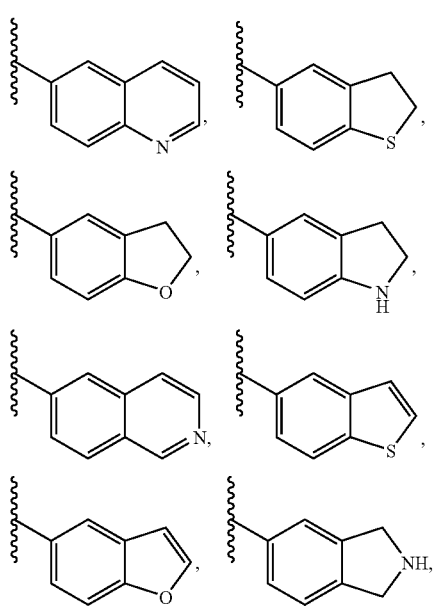

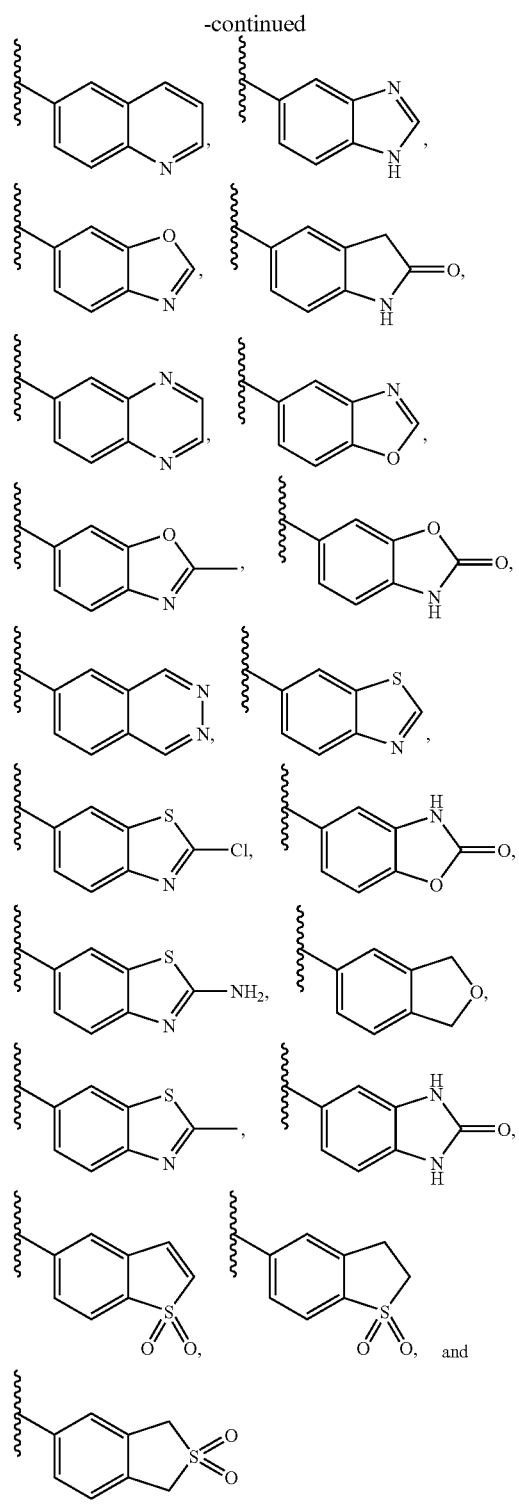

See, for example, Journal of Medicinal Chemistry, 1997, 40 (7), 1049-1058, and references therein; and WO 2002085888.

Synthesis of aryl and heteroaryl acetyl chlorides and aryl and heteroaryl acetic acid hydrazides can also be accessed by methods known in the art (see, Bulletin de la Societe Chimique de France, 1964, 2, 245-247; and Helvitica Chemica Acta, 1928, 11, 609-656). Compound 2-1 is treated with oxalyl chloride in DCM to give Compound 2-2, which is treated with anhydrous hydrazine in DCM to give hydrazide 2-3. Alternatively, Compound 2-1 can be treated with acetic anhydride, followed by hydrazine in water to give Compound 2-3. Acetic acid methyl ester 2-4 can be treated with aqueous hydrazine in ethanol to give Compound 2-3.

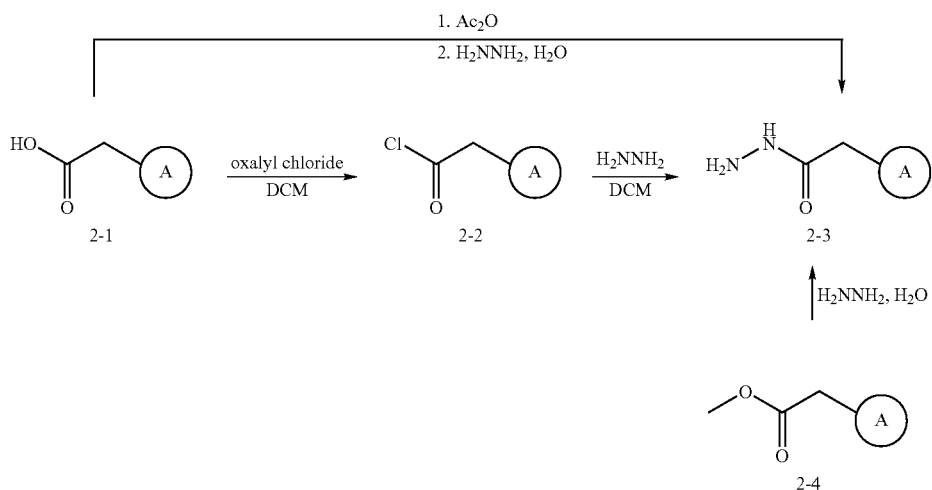

Synthesis of 4-chloro-1H-indole-6-carboxylic acid or 4-fluoro-1H-indole-6-carboxylic acid can be accessed by methods known in the art (see, Chemical and Pharmaceutical Bulletin 1981, 29(11), 3145; and Organic Syntheses, 13, 525, 1933). Compound 3-1 can be treated with hydrochloric acid, sodium nitrite and copper chloride to give Compound 3-2, which can be treated with sodium hydroxide in methanol to give compound 3-3. Alternatively, Compound 3-1 can be treated with hydrochloric acid, sodium nitrite and tetrafluoroboric acid in water and ethanol to give Compound 3-4, which can be treated with sodium hydroxide in methanol to give Compound 3-5.

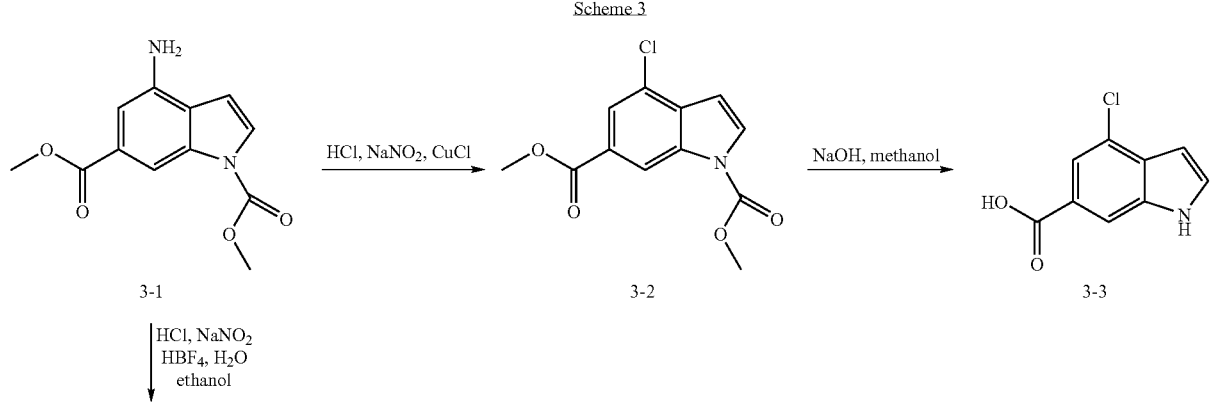

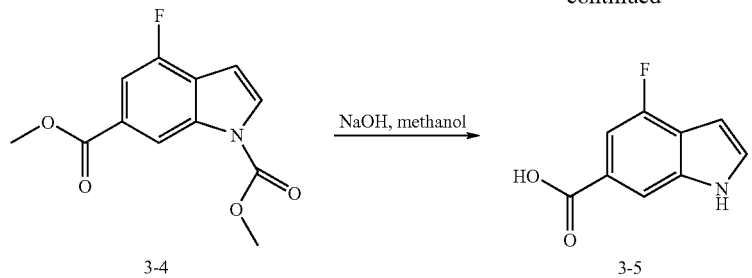

Synthesis of 3,3-dibromo-1,3-dihydro-indol-2-ones can be accomplished by methods known in the art (see, Tetrahedron Letters, 1987, 28 (35), 4027-30). Triethylamine and HBTU are added to a solution of Compound 4-1 in DMF, followed by addition of an amine to give Compound 4-2; a cyclic amine is pictured, for illustrative purposes only; the amine might also be an alkyl amine or a substituted alkyl amine. Compound 4-2 is treated with pyridinium tribromide in aqueous t-butanol to give Compound 4-3. Alternatively, triethylamine and HBTU are added to a solution of Compound 4-1 in DMF, followed by addition of an hydroxyl substituted alkyl amine to give Compound 4-4. Methanesulfonyl chloride is added at 0° C. to a solution of Compound 4-4 in THF and triethylamine, followed by the addition of an amine Z-H at room temperature to give Compound 4-5. This can be further reacted with pyridinium tribromide in aqueous t-butanol to give Compound 4-3.

wherein Z is a nucleophile selected from $NH_2$, NH(alkyl), $N(alkyl)_2$, and

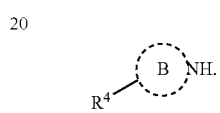

Synthesis substituted 1H-indole-2,3-diones can be accomplished by methods known in the art (see, Tetrahedron Letters, 1984, 25 (29), 3099-3100). Compound 5-1 (also Compound 4-3) is dissolved in a solution of methanol and water and heated to reflux for several hours to give compound 5-2.

Scheme 4

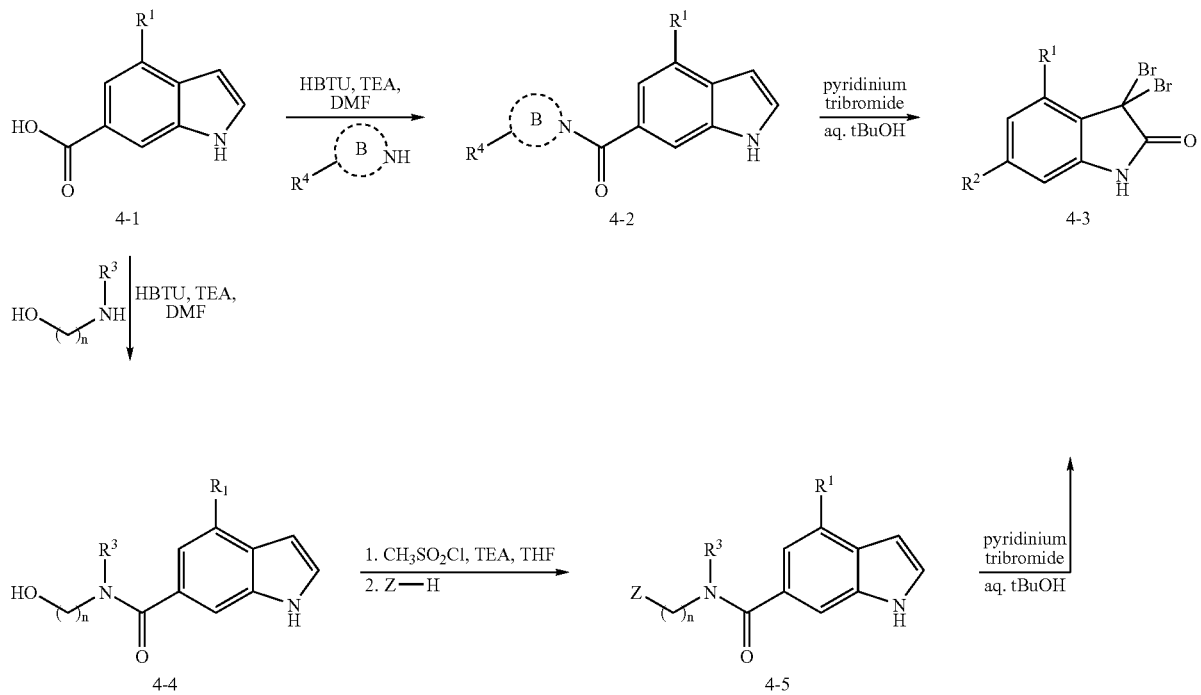

Scheme 5

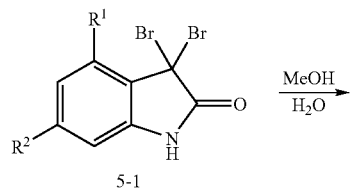
5-1

MeOH / H$_2$O →

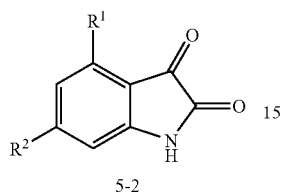
5-2 also Compound 4-3

Synthesis of 3-hydrazono-1,3-dihydro-indol-2-ones can be accessed by methods known in the art (see, European Journal of Medicinal Chemistry 1983, 18 (3), 261-267.). A solution of Compound 6-1 (also Compound 4-3) in THF is treated with aqueous hydrazine at room temperature to give compound 6-2.

Scheme 6

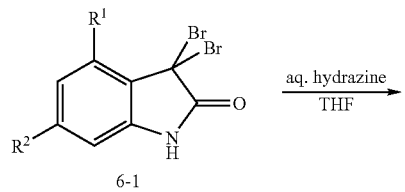
6-1 aq. hydrazine / THF →

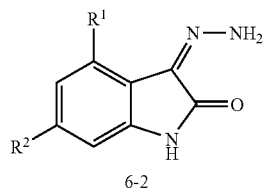
6-2 also Compound 4-3

Synthesis of 1H-Indole-2,3-diones can be accessed by methods known in the art (see, Journal of Organic Chemistry, 1956, 21, 171-173; and Tetrahedron Letters, 1998, 39 (42), 7679-7682). Triethylamine and HBTU can be added to a solution of Compound 7-1 (see, Synthesis, 1998, 11, 1599-1603; Journal of Agricultural and Food Chemistry, 1969, 17, 83-85; and WO 2004050619) in DMF, followed by addition of an amine to give Compound 7-2 (a cyclic amine is pictured, for illustrative purposes only; the amine might also be an alkyl amine or a substituted alkyl amine). Compound 7-2 can be treated with trichloroacetaldehyde, hydroxylamine hydrochloride and sodium sulfate in water, followed by treatment with sulfuric acid to give Compound 7-3. Alternatively, triethylamine and HBTU can be added to a solution of Compound 7-1 in DMF, followed by addition of an hydroxyl substituted alkyl amine to give Compound 7-4. Methanesulfonyl chloride can be added at 0° C. to a solution of Compound 7-4 in THF and triethylamine, followed by the addition of an amine Z-H at room temperature to give Compound 7-5. This can be further reacted with trichloroacetaldehyde, hydroxylamine hydrochloride and sodium sulfate in water, followed by treatment with sulfuric acid to give Compound 7-3.

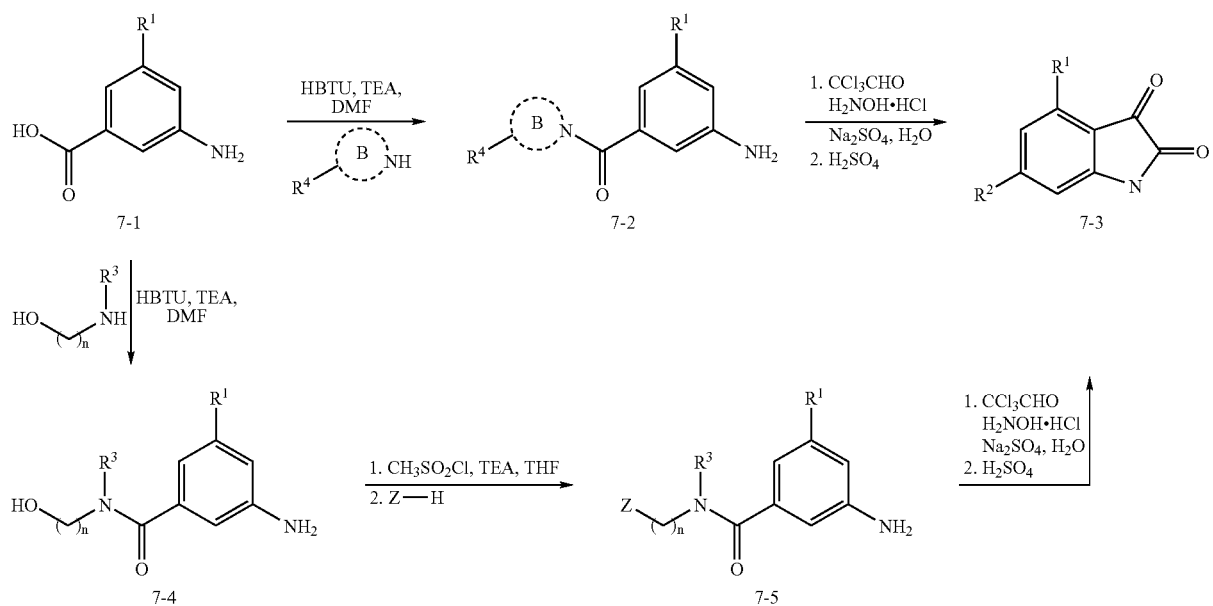

wherein Z is a nucleophile selected from $NH_2$, NH(alkyl), $N(alkyl)_2$, and

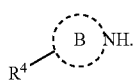

Compounds of Formula I can be accessed by methods known in the art (see, Bioorganic and Medicinal Chemistry Letters 2002, 12 (24) 3601-3604.). One such example is illustrated in Scheme 8. Triethylamine and HBTU are added at room temperature to a solution of acetic acid 2-1 in DMF, followed by addition of Compound 8-1 to give Compound 8-2, an example of Formula I. Alternatively, Compound 8-1 can be added to a solution of triethylamine and THF, followed by addition of acetyl chloride 2-2 to give Compound 8-2. Compounds of Formula I in which the A ring is a benzo[d]isoxazol-3-ylamine can be synthesized in the following manner: Compound 8-1 is treated with triethylamine, Compound 1-6 and HBTU in DMF to give Compound 8-3. Further reaction with acetohydroxamic acid and potassium carbonate in DMF gives Compound 8-2.

An alternative method of accessing compounds of Formula I is illustrated in Scheme 9. Compound 9-1 is heated to reflux in a solution of acetic acid hydrazide 2-3, p-toluenesulfonic acid and ethanol to give Compound 9-2, an example of Formula I.

Scheme 9

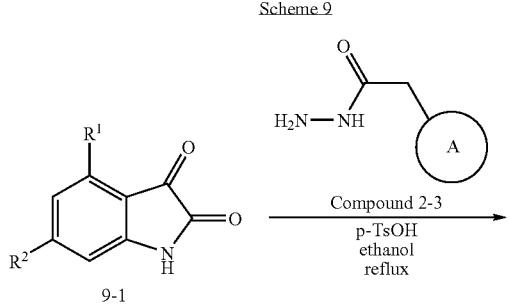

Scheme 8

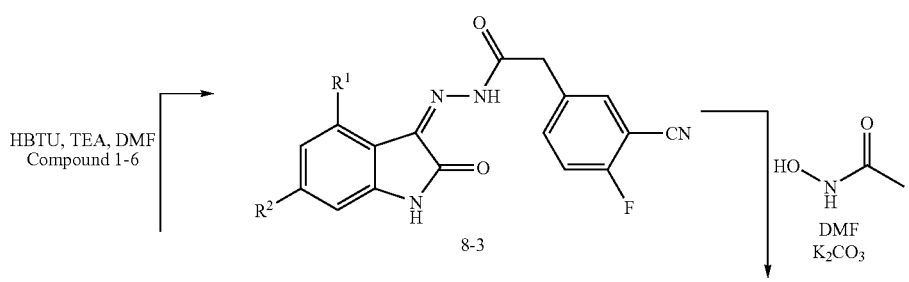

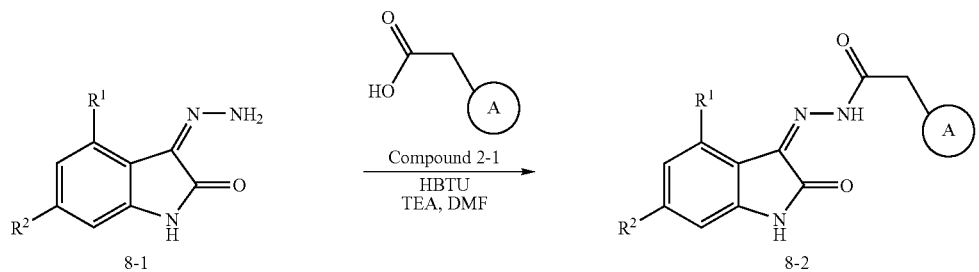

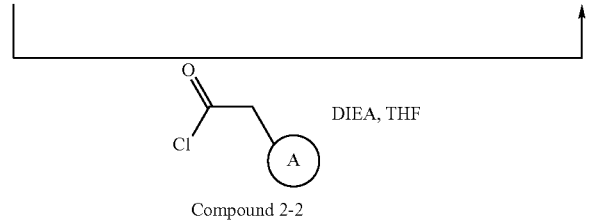

-continued

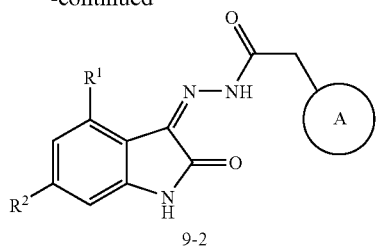
9-2

Representative Compounds

Representative compounds of the present invention synthesized by the aforementioned methods are presented below. Examples of the synthesis of specific compounds are presented thereafter. Preferred compounds are numbers 2, 5, 6, 7, 8, 9, 10, 11, 12, and 14; more preferred compounds are numbers 2, 5, 8, 9, and 11; most preferred compounds are numbers 5, 8, and 11.

| Example Number | Structure |
|---|---|
| 1 | 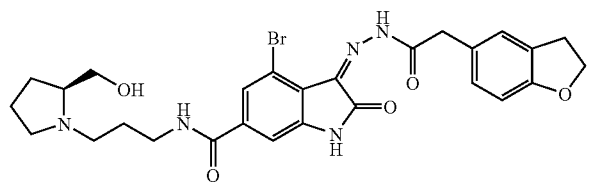 |
| 2 | 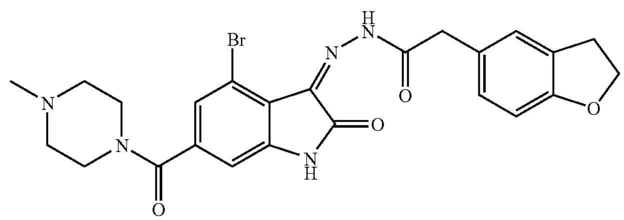 |
| 3 | 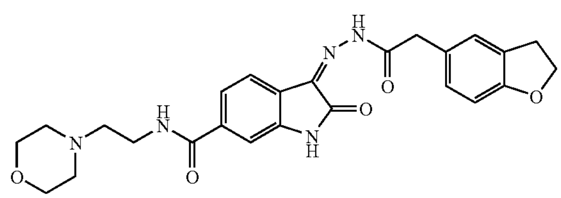 |
| 4 | 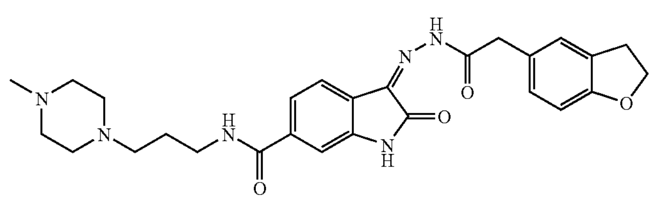 |
| 5 | 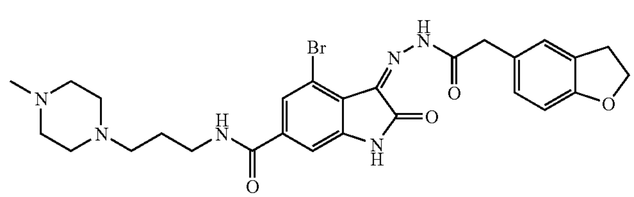 |
| 6 | 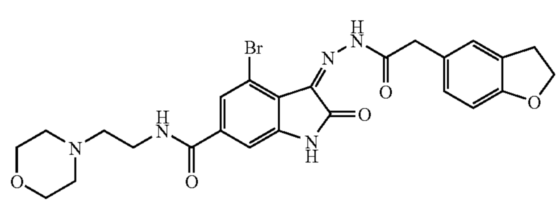 |

-continued
| Example Number | Structure |
|---|---|
| 7 | 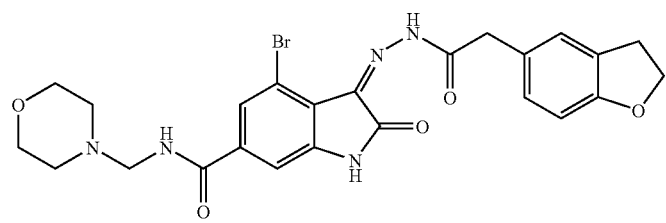 |
| 8 | 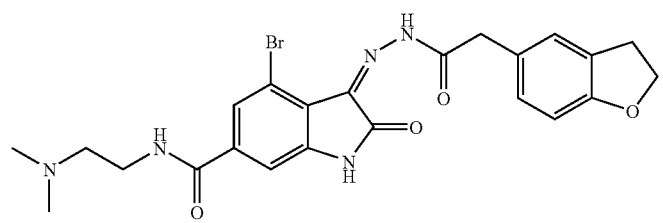 |
| 9 | 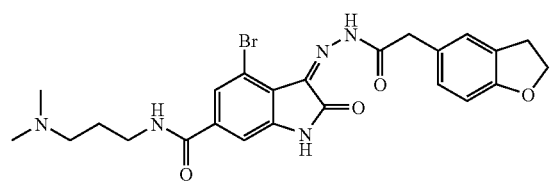 |
| 10 | 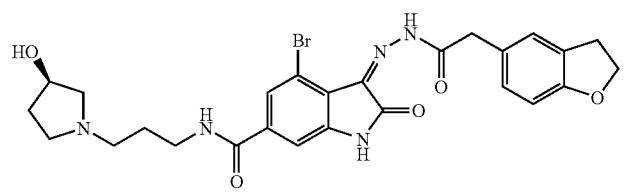 |
| 11 | 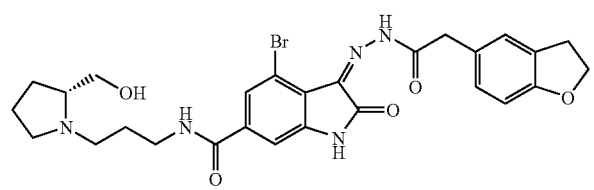 |
| 12 | 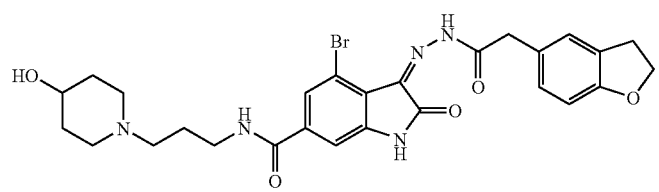 |
| 13 | 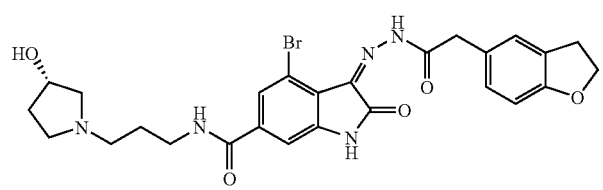 |

-continued
| Example Number | Structure |
|---|---|
| 14 | 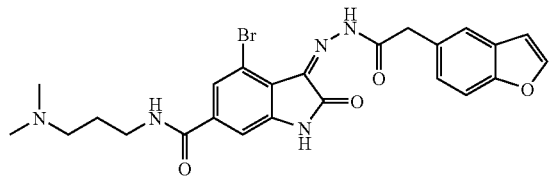 |
| 15 | 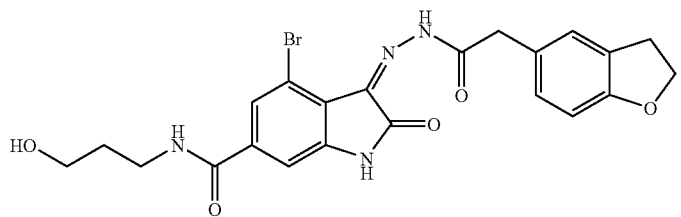 |
| 16 | 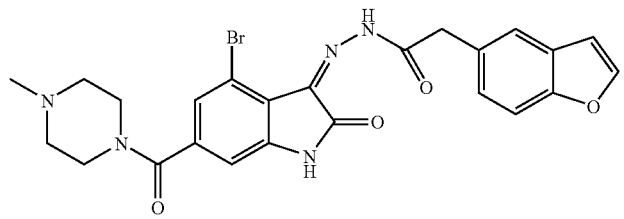 |
| 17 | 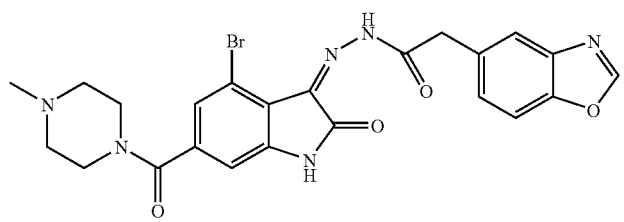 |
| 18 | 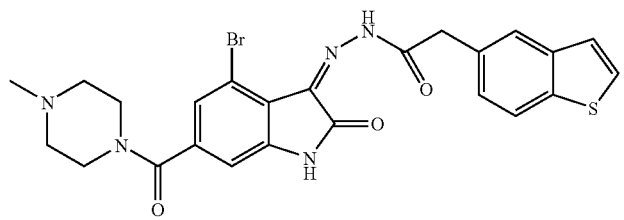 |
| 19 | 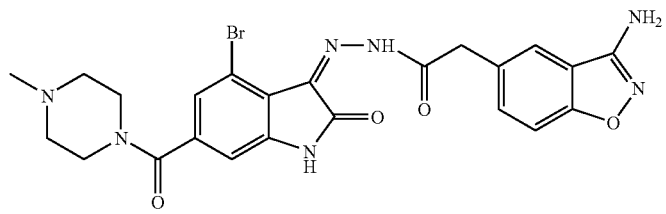 |

EXAMPLE 1

(S)-4-Bromo-3-[(2-2,3-dihydro-benzofuran-5-yl-acetyl)-hydrazono]-2-oxo-2,3-dihydro-1H-indole-6-carboxylic acid [3-(2-hydroxymethyl-pyrrolidin-1-yl)-propyl]-amide

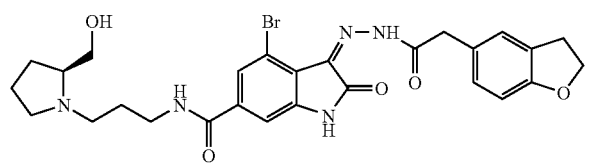

a. 4-Bromo-1H-indole-6-carboxylic acid

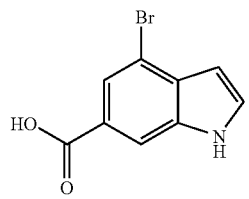

A solution of sodium hydroxide (14.08 g, 352.1 mmol) in water (100 mL) was added a to a solution of 4-bromo-1H-indole-6-carboxylic acid methyl ester in methanol (14.91 mL, 58.7 mmol) at room temperature and stirred for 2.5 hours. The reaction mixture was concentrated in vacuo, 1N HCl was added, and the product was extracted with ethyl acetate to give 13.0 g of 4-bromo-1H-indole-6-carboxylic acid, which was used in the next step with no further purification. $^1$H NMR (400 MHz, CD$_3$OD) δ 8.13 (t, J=1.0 Hz, 1H), 7.87 (d, J=1.3 Hz, 1H), 7.53 (t, J=3.4 Hz, 1H), 8.13 (d, J=4.2 Hz, 1H).

b. 4-Bromo-1H-indole-6-carboxylic acid (3-hydroxy-propyl)-amide

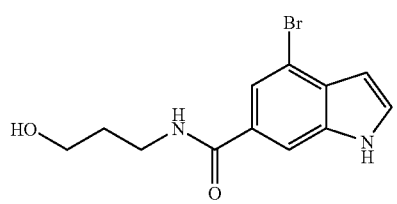

3-Aminopropanol (1.36 g, 18.1 mmol) was added to a solution of 4-bromo-1H-indole-6-carboxylic acid (4.35 g, 18.1 mmol), triethylamine (4.60 mL, 45.3 mmol), and O-benzotriazol-1-yl-N,N,N',N',-tetramethyluronium hexafluorophosphate (HBTU) (6.87 g, 18.1 mmol) in DMF (40 mL) and stirred at room temperature overnight. The reaction mixture was concentrated in vacuo and purified by column chromatography (10% methanol in dichloromethane) to yield 3.0 g (56%) of 4-bromo-1H-indole-6-carboxylic acid (3-hydroxy-propyl)-amide. Mass spectrum (LCMS, ESI pos.): Calcd for C$_{12}$H$_{13}$BrN$_2$O$_2$ 296.02. Found 296.9; (M+H).

c. (S)-4-Bromo-1H-indole-6-carboxylic acid [3-(2-hydroxymethyl-pyrrolidin-1-yl)-propyl]amide

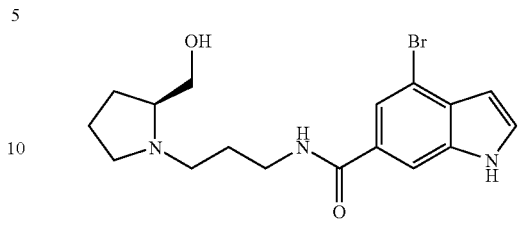

A solution methanesulfonyl chloride (0.13 mL, 1.68 mmol) in THF (1 mL) was added to a solution of 4-bromo-1H-indole-6-carboxylic acid (3-hydroxy-propyl)-amide (0.50 g, 1.68 mmol) and triethylamine (0.25 mL, 1.84 mmol) in tetrahydrofuran (5 mL) at 0° C. and slowly warmed to room temperature over 30 minutes. (S)-(+)-2-pyrrolidinemethanol (1.0 g, 9.88 mmol) was added and stirred at room temperature overnight. The reaction was concentrated in vacuo and purified by column chromatography (5% methanol in dichloromethane) to yield 0.50 g (78%) of (S)-4-bromo-1H-indole-6-carboxylic acid [3-(2-hydroxymethyl-pyrrolidin-1-yl)-propyl]-amide. Mass spectrum (LCMS, ESI pos.): Calcd for C$_{17}$H$_{22}$BrN$_3$O$_2$ 379.09. Found 380.0; (M+H).

d. (S)-4-Bromo-3-hydrazono-2-oxo-2,3-dihydro-1H-indole-6-carboxylic acid [3-(2-hydroxymethyl-pyrrolidin-1-yl)-propyl]-amide

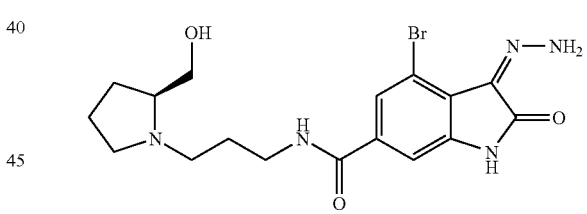

Pyridinium tribromide (1.67 g, 5.2 mmol) was added in several shots at room temperature to a solution of (S)-4-bromo-1H-indole-6-carboxylic acid [3-(2-hydroxymethyl-pyrrolidin-1-yl)-propyl]-amide (0.50 g, 1.30 mmol) dissolved in t-butanol:water (6:1) [7 mL]. The reaction was concentrated in vacuo and taken up in THF and water. Hydrazine hydrate (1 mL) was added to the reaction and the biphasic mixture was stirred at room temperature for 30 minutes. Ethyl acetate was added and the product was extracted to give 0.223 g of (S)-4-bromo-3-hydrazono-2-oxo-2,3-dihydro-1H-indole-6-carboxylic acid[3-(2-hydroxymethyl-pyrrolidin-1-yl)-propyl]-amide, which was used in the next step with no further purification. Mass spectrum (LCMS, ESI pos.): Calcd for C$_{17}$H$_{22}$BrN$_5$O$_3$ 423.09. Found 424.1; (M+H).

e. (S)-4-Bromo-3-[(2-2,3-dihydro-benzofuran-5-yl-acetyl)-hydrazono]-2-oxo-2,3 dihydro-1H-indole-6-carboxylic acid [3-(2-hydroxymethyl-pyrrolidin-1-yl)-propyl]-amide

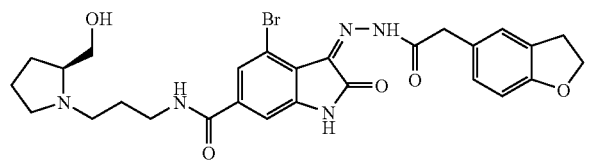

(S)-4-Bromo-3-hydrazono-2-oxo-2,3-dihydro-1H-indole-6-carboxylic acid [3-(2-hydroxymethyl-pyrrolidin-1-yl)-propyl]-amide (0.22 g, 0.52 mmol) was added to a solution of (2,3-dihydro-benzofuran-5-yl)-acetic acid (0.93 g, 0.52 mmol), triethylamine (0.01 mL, 0.78 mmol) and HBTU (0.20 g, 0.52 mmol) in DMF (4 mL) and stirred at room temperature overnight. The reaction mixture was concentrated in vacuo and purified by column chromatography (20% methanol in dichloromethane) followed by HPLC (10-100% acetonitrile/water) to give 0.040 g (13%) of (S)-4-bromo-3-[(2-2,3-dihydro-benzofuran-5-yl-acetyl)-hydrazono]-2-oxo-2,3-dihydro-1H-indole-6-carboxylic acid [3-(2-hydroxymethyl-pyrrolidin-1-yl)-propyl]-amide. $^1$H NMR (400 MHz, CD$_3$OD) δ 7.75 (s, 1H), 7.37 (s, 1H), 7.24 (s, 1H), 7.11 (d, J=7.8 Hz, 1H), 6.65 (d, J=8.2 Hz, 1H), 4.50 (t, J=12.7 Hz, 2H), 4.10 (bs, 2H), 3.88 (dd, J=3.9 Hz, J=12.2 Hz, 1H), 3.74-3.40 (m, 6H), 3.22-3.04 (m, 4H), 2.26-1.81 (m, 6H). Mass spectrum (LCMS, ESI pos.): Calcd for C$_{27}$H$_{30}$BrN$_5$O$_5$: 584.46. Found 584.1; (M+H).

EXAMPLE 2

(2,3-Dihydro-benzofuran-5-yl)-aceticacid[4-bromo-6-(4-methyl-piperazine-1-carbonyl)-2-oxo-1,2-dihydro-indol-3-ylidene]-hydrazide

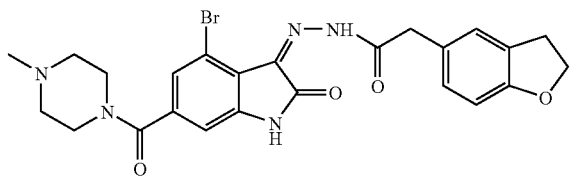

a. 4-Bromo-1H-indol-6-yl)-(4-methyl-piperazin-1-yl)-methanone

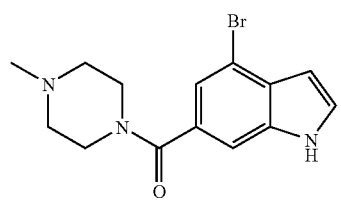

1-Methyl-piperazine (0.21 g, 2.1 mmol) was added to a solution of 4-bromo-1H-indole-6-carboxylic acid (0.50 g, 2.1 mmol), triethylamine (0.43 mL, 3.1 mmol) and HBTU (0.78 g, 2.1 mmol) in DMF (5 mL) and stirred at room temperature overnight. Reaction mixture was concentrated in vacuo and purified by column chromatography (10% methanol in dichloromethane) to yield 0.30 g (45%) of (4-bromo-1H-indol-6-yl)-(4-methyl-piperazin-1-yl)-methanone. Mass spectrum (LCMS, ESI pos.): Calcd for C$_{14}$H$_{16}$BrN$_3$O: 321.05. Found 322.0 ; (M+H).

b. (2,3-Dihydro-benzofuran-5-yl)-acetic acid [4-bromo-6-(4-methyl-piperazine-1carbonyl)-2-oxo-1,2-dihydro-indol-3-ylidene]-hydrazide

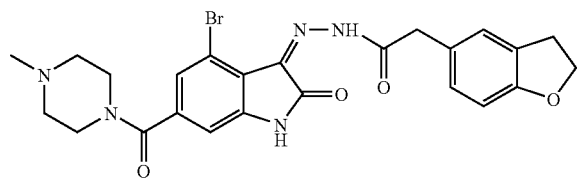

The title compound was synthesized using the same procedure as example 1, steps d-e. $^1$H NMR (400 MHz, CD$_3$OD) δ 7.44 (s, 1H), 7.28 (s, 1H), 7.14 (d, J=8.1 Hz, 1H), 7.04 (s, 1H), 6.67 (d, J=7.9 Hz, 1H), 4.53 (t, J=7.9 Hz, 2H), 4.16 (bs, 2H), 3.90-3.36 (m, 8H), 3.22-3.14 (m, 2H), 2.97 (s, 3H). Mass spectrum (LCMS, ESI pos.): Calcd for C$_{24}$H$_{24}$BrN$_5$O$_4$: 525.10. Found 526.1 (M+H).

EXAMPLE 3

3-[(2-2,3-Dihydro-benzofuran-5-yl-acetyl)-hydrazono]-2-oxo-2,3-dihydro-1H-indole-6-carboxylic acid(2-morpholin-4-yl-ethyl)-amide

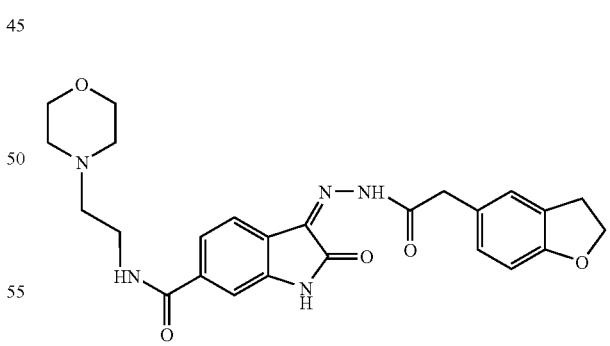

The title compound was synthesized using the same procedure as example 2. $^1$H NMR (400 MHz, CD$_3$OD) δ 7.85-7.75 (m, 1H), 7.70-7.55 (m, 1H), 7.44 (d, J=12.7 Hz, 1H), 7.24 (s, 1H), 7.10 (d, J=8.3 Hz, 1H), 6.78-6.63 (m, 1H), 4.64-4.48 (m, 2H), 4.10 (bs, 2H), 3.91-3.6 (m, 6H), 3.51-3.37 (m, 2H), 3.31-3.10 (m, 6H). Mass spectrum (LCMS, ESI pos.): Calcd for C$_{25}$H$_{27}$N$_5$O$_5$ 477.20. Found 478.1; (M+H).

EXAMPLE 4

3-[(2-2,3-Dihydro-benzofuran-5-yl-acetyl)-hydrazono]-2-oxo-2,3-dihydro-1H-indole-6-carboxylic acid [3-(4-methyl-piperazin-1-yl)-propyl]-amide

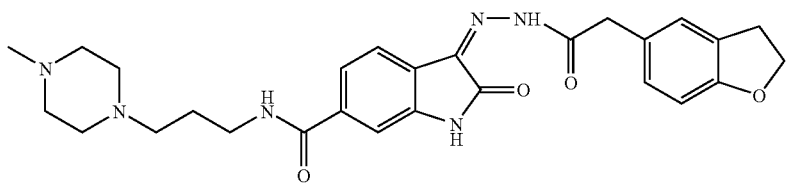

The title compound was synthesized using the same procedure as example 2. $^1$H NMR (400 MHz, CD$_3$OD) δ 7.83-7.70 (m, 1H), 7.64-7.52 (m, 1H), 7.40 (d, J=11.6 Hz, 1H), 7.23 (s, 1H), 7.10 (d, J=8.3 Hz, 1H), 6.79-6.64 (m, 1H), 4.61-4.47 (m, 2H), 4.10 (s, 1H), 3.75 (s, 1H), 3.55-3.35 (m, 10H), 3.27-3.15 (m, 2H), 3.12-3.01 (m, 2H), 2.93 (s, 3H), 2.06-1.95 (m, 2H). Mass spectrum (LCMS, ESI pos.): Calcd for C$_{27}$H$_{32}$N$_6$O$_4$: 504.25. Found 505.3 (M+H).

EXAMPLE 5

4-Bromo-3-[(2-2,3-dihydro-benzofuran-5-yl-acetyl)-hydrazono]-2-oxo-2,3-dihydro-1H-indole-6-carboxylic acid [3-(4-methyl-piperazin-1-yl)-propyl]-amide

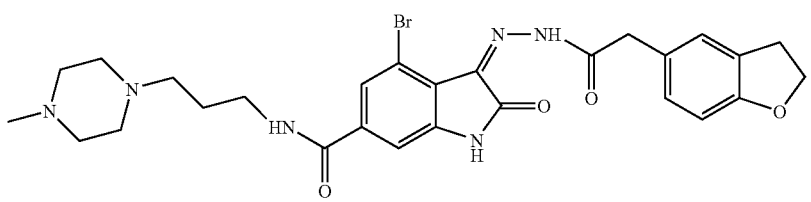

The title compound was synthesized using the same procedure as example 2. $^1$H NMR (400 MHz, CD$_3$OD) δ 7.75 (s, 1H), 7.39 (s, 1H), 7.27 (s, 1H), 7.13 (d, J=8.1 Hz, 1H), 6.67 (d, J=7.90 Hz, 1H), 4.51 (t, J=8.7 Hz, 2H), 4.14 (s, 2H), 3.64-3.44 (m, 10H), 3.25-3.14 (m, 4H), 2.97 (s, 3H), 2.12-1.99 (m, 2H). Mass spectrum (LCMS, ESI pos.): Calcd for C$_{27}$H$_{31}$BrN$_6$O$_4$: 582.16. Found 583.3; (M+H).

EXAMPLE 6

4-Bromo-3-[(2-2,3-dihydro-benzofuran-5-yl-acetyl)-hydrazono]-2-oxo-2,3-dihydro-1H-indole-6-carboxylic acid (2-morpholin-4-yl-ethyl)-amide

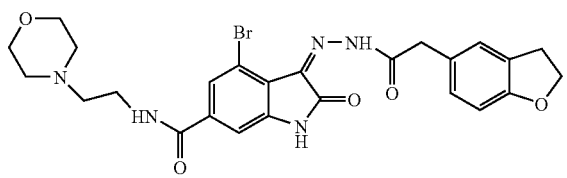

The title compound was synthesized using the same procedure as example 2. $^1$H NMR (400 MHz, CD$_3$OD) δ 7.84 (s, 1H), 7.45 (s, 1H), 7.27 (s, 1H), 7.15 (d, J=7.9 Hz, 1H), 6.67 (d, J=8.3 Hz, 1H), 4.53 (t, J=8.6 Hz, 2H), 4.20-4.05 (m, 4H), 3.85-3.58 (m, 6H), 3.43 (t, J=5.6 Hz, 2H), 3.27-3.12 (m, 4H). Mass spectrum (LCMS, ESI pos.): Calcd for C$_{25}$H$_{26}$BrN$_5$O$_5$: 555.11. Found 556.1; (M+H).

EXAMPLE 7

4-Bromo-3-[(2-2,3-dihydro-benzofuran-5-yl-acetyl)-hydrazono]-2-oxo-2,3-dihydro-1H-indole-6-carboxylic acid (3-morpholin-4-yl-propyl)-amide

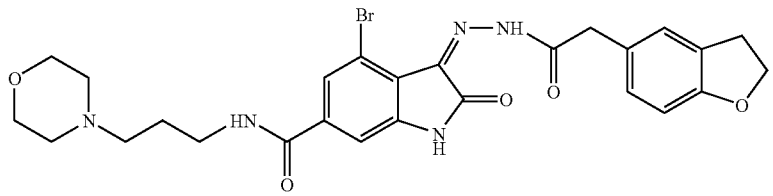

The title compound was synthesized using the same procedure as example 2. $^1$H NMR (400 MHz, CD$_3$OD) δ 7.80 (s, 1H), 7.41 (s, 1H), 7.27 (s, 1H), 7.15 (d, J=6.9 Hz, 1H), 6.68 (d, J=6.9 Hz, 1H), 4.54 (t, J=8.7 Hz, 2H), 4.19-4.06 (0, 4H), 3.79 (t, J=12.4 Hz, 2H), 3.57-3.47 (m, 4H), 3.30-3.12 (m, 6H), 2.15-2.04 (m, 2H). Mass spectrum (LCMS, ESI pos.): Calcd for C$_{26}$H$_{28}$BrN$_5$O$_5$: 569.13. Found 570.1; (M+H).

EXAMPLE 8

4-Bromo-3-[(2-2,3-dihydro-benzofuran-5-yl-acetyl)-hydrazono]-2-oxo-2,3-dihydro-1H-indole-6-carboxylic acid (2-dimethylamino-ethyl)-amide

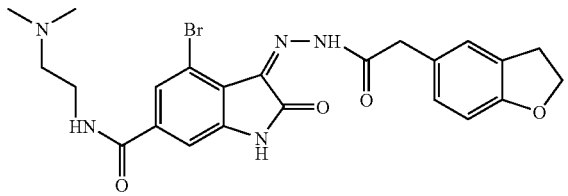

The title compound was synthesized using the same procedure as example 2. $^1$H NMR (400 MHz, CD$_3$OD) δ 7.82 (s, 1H), 7.44 (s, 1H), 7.27 (s, 1H), 7.15 (d, J=7.6 Hz, 1H), 6.68 (d, J=7.6 Hz, 1H), 4.53 (t, J=8.6 Hz, 2H), 4.16 (bs, 2H), 3.77 (t, J=5.8 Hz, 2H), 3.40 (t, J=5.8 Hz, 2H), 3.23-3.14 (m, 2H), 3.00 (s, 6H). Mass spectrum (LCMS, ESI pos.): Calcd for C$_{23}$H$_{24}$BrN$_5$O$_4$; 513.10. Found 514.0; (M+H).

EXAMPLE 9

4-Bromo-3-[(2-2,3-dihydro-benzofuran-5-yl-acetyl)-hydrazono]-2-oxo-2,3-dihydro-1H-indole-6-carboxylic acid (3-dimethylamino-propyl)-amide

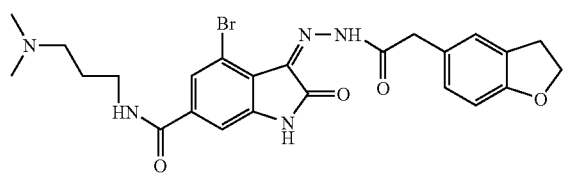

The title compound was synthesized using the same procedure as example 2. $^1$H NMR (400 MHz, CD$_3$OD) δ 7.78 (s, 1H), 7.40 (s, 1H), 7.26 (s, 1H), 7.13 (d, J=7.2 Hz, 1H), 6.67 (d, J=7.2 Hz, 1H), 4.53 (t, J=8.7 Hz, 2H), 4.15 (bs, 2H), 3.49 (t, J=6.0 Hz, 2H), 3.24-3.12 (m, 4H), 2.91 (s, 6H), 2.10-1.98 (m, 2H). Mass spectrum (LCMS, ESI pos.): Calcd for C$_{24}$H$_{26}$BrN$_5$O$_4$: 527.12. Found 528.1 (M+H).

EXAMPLE 10

(R)-4-Bromo-3-[(2-2,3-dihydro-benzofuran-5-yl-acetyl)-hydrazono]-2-oxo-2,3-dihydro-1H-indole-6-carboxylic acid [3-(3-hydroxy-pyrrolidin-1-yl)-propyl]-amide

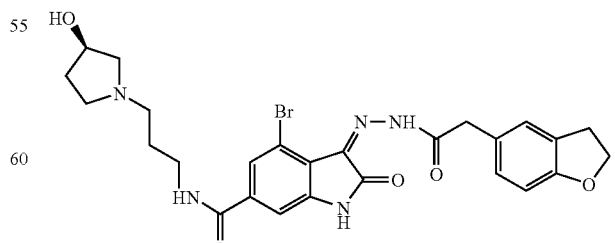

The title compound was synthesized using the same procedure as example 1. $^1$H NMR (400 MHz, CD$_3$OD) δ 7.80 (s, 1H), 7.43 (s, 1H), 7.28 (s,1H), 7.14 (d, J=8.6 Hz, 1H), 6.68 (d, J=8.3 Hz, 1H), 4.61-4.48 (m, 3H), 4.16 (bs, 2H), 3.87-3.73 (m, 2H), 3.60-3.46 (m, 4H), 3.25-3.10 (m, 4H), 2.44-2.30 (m, 1H), 2.17-2.10 (m, 1H), 2.08-2.00 (m, 2H). Mass spectrum (LCMS, ESI pos.): Calcd for $C_{26}H_{28}BrN_5O_5$: 569.13. Found 570.1; (M+H).

EXAMPLE 11

(R)-4-Bromo-3-[(2-2,3-dihydro-benzofuran-5-yl-acetyl)-hydrazono]-2-oxo-2,3-dihydro-1H-indole-6-carboxylic acid [3-(2-hydroxymethyl-pyrrolidin-1-yl)-propyl]-amide

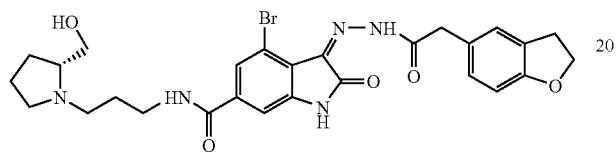

The title compound was synthesized using the same procedure as example 1. $^1$H NMR (400 MHz, CD$_3$OD) δ 7.75 (s, 1H), 7.37 (s, 1H), 7.24 (s, 1H), 7.11 (d, J=7.82 Hz, 1H), 6.65 (d, J=8.2 Hz, 1H), 4.50 (t, J=12.7 Hz, 2H), 4.10 (bs, 2H), 3.88 (dd, J=3.9 Hz, J=12.5 Hz, 1H), 3.74-3.40 (m, 6H), 3.22-3.04 (m, 4H), 2.26-1.81 (m, 6H). Mass spectrum (LCMS, ESI pos.): Calcd for $C_{27}H_{30}BrN_5O_5$: 583.14. Found 584.1; (M+H).

EXAMPLE 12

4-Bromo-3-[(2-2,3-dihydro-benzofuran-5-yl-acetyl)-hydrazono]-2-oxo-2,3-dihydro-1H-indole-6-carboxylic acid [3-(4-hydroxy-piperidin-1-yl)-propyl]-amide

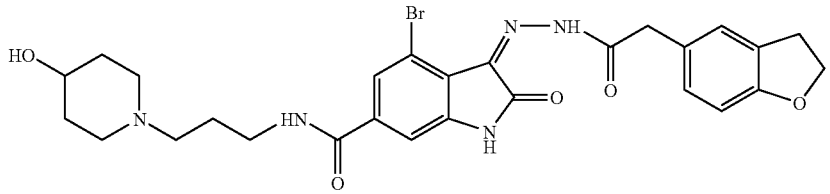

The title compound was synthesized using the same procedure as example 1. $^1$H NMR (400 MHz, CD$_3$OD) δ 7.75 (s, 1H), 7.36 (s, 1H), 7.24 (s, 1H), 7.25 (s, 1H), 7.12 (d, J=7.8 Hz, 1H), 6.65 (d, J=7.4 Hz, 1H), 4.50 (t, J=8.6 Hz, 2H), 4.19-4.04 (m, 2H), 3.89 3.72 (m, 1H), 3.64-3.34 (m, 4H), 3.23-2.96 (m, 6H), 2.18-1.89 (m, 5H), 1.78-1.64 (m, 1H). Mass spectrum (LCMS, ESI pos.): Calcd for $C_{27}H_{30}BrN_5O_5$: 583.14. Found 584.1 (M+H).

EXAMPLE 13

(S)-4-Bromo-3-[(2-2,3-dihydro-benzofuran-5-yl-acetyl)-hydrazono]-2-oxo-2,3-dihydro-1H-indole-6-carboxylic acid [3-(3-hydroxy-pyrrolidin-1-yl)-propyl]-amide

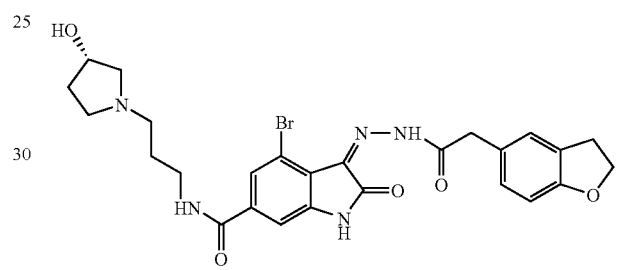

The title compound was synthesized using the same procedure as example 1. $^1$H NMR (400 MHz, CD$_3$OD) δ 7.80 (s, 1H), 7.43 (s, 1H), 7.28 (s,1H), 7.14 (d, J=7.8 Hz, 1H), 6.68 (m, 1H), 4.60-4.43 (m, 3H), 4.14 (bs, 2H), 3.85-3.70 (m, 2H), 3.62-3.40 (m, 4H), 3.19-3.06 (m, 4H), 2.44-2.25 (m, 1H), 2.15-1.95 (m, 1H), 2.08-2.00 (m, 2H). Mass spectrum (LCMS, ESI pos.): Calcd for $C_{26}H_{28}BrN_5O_5$: 569.13. Found 570.1; (M+H).

EXAMPLE 14

3-[(2-Benzofuran-5-yl-acetyl)-hydrazono]-4-bromo-2-oxo-2,3-dihydro-1H-indole-6-carboxylic acid (3-dimethylamino-propyl)-amide

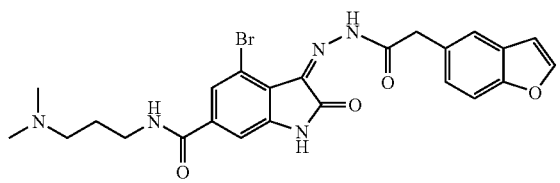

a. benzofuran-5-yl-acetic acid

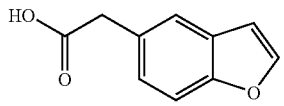

N-bromosuccinimide (0.89 g, 5.0 mmol) was added to a solution of 2,3-dihydrobenzofuran-5-ylacetic acid (0.89 g, 5.0 mmol) and benzoyl peroxide (10 mg) in carbon tetrachloride (100 mL) and refluxed for 3 hours. The mixture was cooled to room temperature, filtered and concentrated. The product was recrystallized from ethyl acetate:hexane (2:1) to give a 0.39 g (44%) of white solid. $^1$H NMR (400 MHz, CD$_3$OD) δ 7.62 (d, J=2.4 Hz, 1H), 7.52 (d, J=0.8 Hz, 1H), 7.46 (d, J=8.4 Hz, 1H), 7.21 (dd, J=1.6, 8.4 Hz, 1H), 6.74 (d, J=3.2 Hz, 1H), 3.74 (s, 2H).

b. 3-[(2-Benzofuran-5-yl-acetyl)-hydrazono]-4-bromo-2-oxo-2,3-dihydro-1H-indole-6-carboxylic acid (3-dimethylamino-propyl)-amide

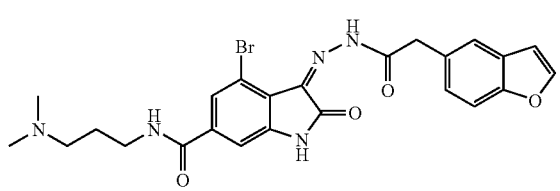

The title compound was synthesized using the same procedure as example 2. $^1$H NMR (400 MHz, CD$_3$OD) δ 7.78 (s, 1H), 7.72 (s, 1H), 7.66 (s, 1H), 7.43 (m, 2H), 7.34 (m, 1H), 6.79 (s, 1H), 4.31 (s, 2H), 3.49 (t, J=7.6 Hz, 2H), 3.19 (t, J=7.6 Hz, 2H), 2.89 (s, 6H), 2.04 (m, 2H). Mass spectrum (LCMS, ESI pos.): Calcd for C$_{24}$H$_{24}$BrN$_5$O$_4$: 525.1. Found 526.1 (M+H).

EXAMPLE 15

4-Bromo-3-[(2-2,3-dihydro-benzofuran-5-yl-acetyl)-hydrazono]-2-oxo-2,3-dihydro-1H-indole-6-carboxylic acid (3-hydroxy-propyl)-amide

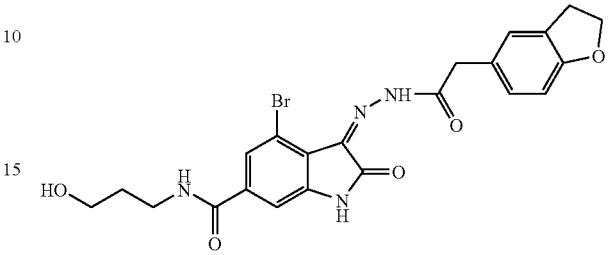

The title compound was synthesized using the same procedure as example 1. $^1$H NMR (400 MHz, DMSO) δ 12.70 (bs, 1H), 11.60 (s,1H), 8.64 (t, J=5.1 Hz, 1H), 7.78 (s, 1H), 7.37 (s, 1H), 7.23 (s,1H), 7.09 (d, J=8.3 Hz, 1H), 6.70 (d, J=8.1 Hz, 1H), 4.53-4.45 (m, 3H), 4.08 (bs, 2H), 3.50-3.42 (m, 2H), 3.15 (t, J=8.62 Hz, 2H), 1.68 (q, J=6.6, J=13.2 Hz, 2H), 1.31-1.18 (m, 2H). Mass spectrum (LCMS, ESI pos.): Calcd for C$_{22}$H$_{21}$BrN$_4$O$_5$: 500.07. Found 500.9 (M+H).

EXAMPLE 16

Benzofuran-5-yl-acetic acid [4-bromo-6-(4-methyl-piperazine-1-carbonyl)-2-oxo-1,2-dihydro-indol-3-ylidene]-hydrazide hydrochloride

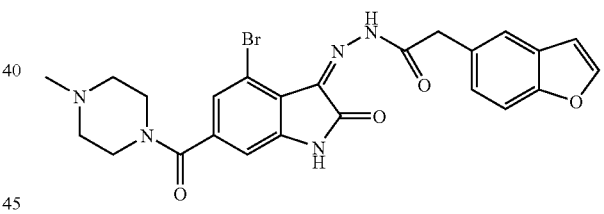

a) Benzofuran-5-yl-acetic acid

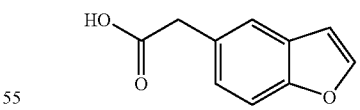

To the solution of (2,3-dihydro-benzofuran-5-yl)-acetic acid (0.89 g, 5 mmol) and N-bromosuccinimide (0.89 g, 5 mmol) in carbon tetrachloride (10 mL) was added 10 mg of benzoyl peroxide. The mixture was refluxed for 3 h and cooled with ice. The solid was removed by filtration, the filtrate was concentrated, the residue was crystallized from 1:1 ethyl acetate:hexane to give a white solid (390 mg, 44%). $^1$H NMR (400 MHz, CDCl$_3$) δ 10.5 (b s, 1H), 7.62 (d, J=2.2 Hz, 1H), 7.52 (d, J=1.4 Hz, 1H), 7.46 (d, J=8.4 Hz, 1H), 7.21 (dd, J=8.4, 1.8 Hz, 1H), 6.74 (d, J=2.2 Hz, 1H), 3.75 (s, 2H).

b) Benzofuran-5-yl-acetic acid [4-bromo-6-(4-methyl-piperazine-1-carbonyl)-2-oxo-1,2-dihydro-indol-3-ylidene]-hydrazide hydrochloride

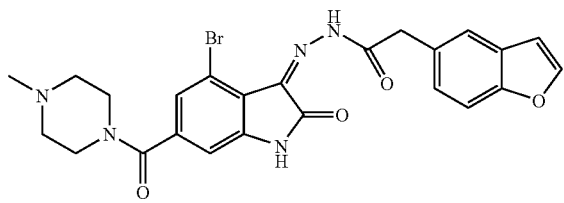

The title compound was synthesized using the same procedure as in Example 2. $^1$H NMR (400 MHz, CD$_3$OD) δ 7.72 (s, 1H), 7.66 (s, 1H), 7.44 (d, J=7.6 Hz, 1H), 7.42 (s, 1H), 7.35 (d, J=7.8 Hz, 1H), 7.02 (s, 1H), 6.79 (s, 1H), 4.32 (br s, 2H), 3.55 (m, 4H), 3.22 (m, 4H), 2.95 (s, 3H). Mass spectrum (LCMS, ESI pos.): Calcd for C$_{24}$H$_{22}$BrN$_5$O$_4$: 523.1. Found: 524.1 (M+H).

EXAMPLE 17

Benzooxazol-5-yl-acetic acid [4-bromo-6-(4-methyl-piperazine-1-carbonyl)-2-oxo-1,2-dihydro-indol-3-ylidene]-hydrazide

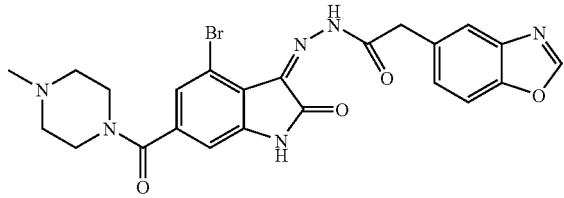

a) Benzooxazol-5-yl-acetic acid

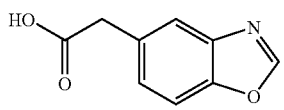

The mixture of (3-amino-4-hydroxy-phenyl)-acetic acid (250 mg, 1.5 mmol) and triethyl orthoformate (30 mg, 2.0 mmol) in toluene was refluxed for 3 h, cooled to room temperature and concentrated. The resulting solid was collected, washed with 1:3 ethyl acetate:hexane and dried to give the title compound (220 mg, 83%). $^1$H NMR (400 MHz, DMSO) δ 12.4 (b s, 1H), 8.70 (s, 1H), 7.68 (d, J=6.7 Hz, 1H), 7.66 (s, 1H), 7.31 (d, J=6.8 Hz, 1H), 3.33 (s, 2H). Mass spectrum (LCMS, ESI pos.): Calcd for C$_9$H$_7$NO$_3$: 177.2. Found: 178.2 (M+H).

b) Benzooxazol-5-yl-acetic acid [4-bromo-6-(4-methyl-piperazine-1-carbonyl)-2-oxo-1,2-dihydro-indol-3-ylidene]-hydrazide

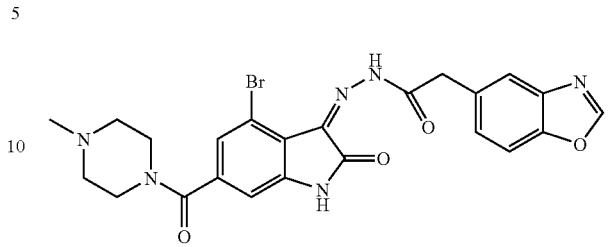

The title compound was synthesized using the same procedure as in Example 2. $^1$H NMR (400 MHz, DMSO) δ 12.73 (br s, 1H), 11.58 (br s 1H), 8.71(s, 1H), 7.80 (s, 1H), 7.71 (d, J=8.3 Hz, 1H), 7.43 (d, J=8.4 Hz, 1H), 7.29 (s, 1H), 6.90 (s, 1H), 4.30 (br s, 1H), 3.60 (m, 4H), 3.40 (m, 4H), 3.10 (s, 3H). Mass spectrum (LCMS, ESI pos.): Calcd for C$_{23}$H$_{21}$BrN$_6$O$_4$: 524.1. Found: 525.0; (M+H).

EXAMPLE 18

Benzothiophen-5-yl-acetic acid [4-bromo-6-(4-methyl-piperazine-1-carbonyl)-2-oxo-1,2-dihydro-indol-3-ylidene]-hydrazide hydrochloride

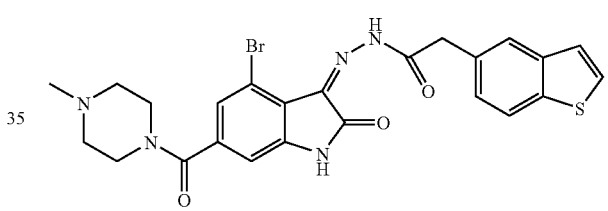

The title compound was synthesized using the same procedure as in Example 2 (benzothiophen-5-yl-acetic acid was prepared according to Meyer, M. D., Hancock, A. A., et al., *J. Med. Chem.* 1997, 40 (7), 1049-1062). $^1$H NMR (400 MHz, DMSO) δ 12.75 (s, 1H), 11.76 (br s, 1H), 11.24 (br s, 1H), 7.96 (m, 1H), 7.89 (s, 1H), 7.76 (d, J=5.5 Hz, 1H), 7.42 (d, J=5.4 Hz, 1H), 7.39 (m, 2H), 7.00 (s, 1H), 6.79 (s, 1H), 4.30 (br s, 2H), 3.51 (m, 4H), 3.09 (m, 4H), 2.75 (s, 3H). Mass spectrum (LCMS, ESI pos.): Calcd for C$_{24}$H$_{22}$BrN$_5$OS: 540.2; found: 540.1 (M+H).

EXAMPLE 19

(3-Amino-benzo[d]isoxazol-5-yl)-acetic acid [4-bromo-6-(4-methyl-piperazine-1-carbonyl)-2-oxo-1,2-dihydro-indol-3-ylidene]-hydrazide

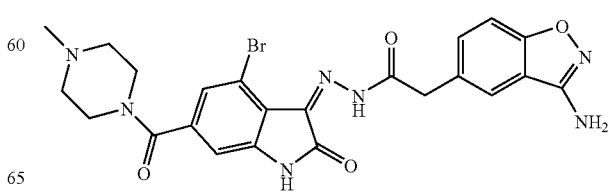

a) (3-Cyano-4-fluoro-phenyl)-acetic acid

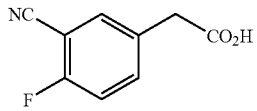

The title compound was prepared as a yellow solid from 3-bromo-4-fluorophenylacetic acid using the method of deSolms et al. (*J. Med. Chem.* 2003, 46 (14), 2980). $^1$H NMR (400 MHz, DMSO-$d_6$) δ 12.6 (bs, 1H), 7.80 (dd, J=6.3 Hz, 2.4 Hz, 1H), 7.66 (m, 1H), 7.46 (t, J=9 Hz, 1H), 3.66 (s, 2H).

b) (3-Cyano-4-fluoro-phenyl)-acetic acid [4-bromo-6-(4-methyl-piperazine-1-carbonyl)-2-oxo-1,2-dihydro-indol-3-ylidene]-hydrazide

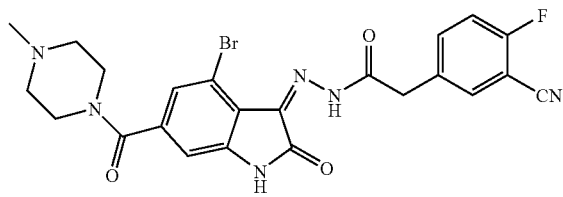

The title compound was prepared as an orange solid, from the product of the preceding step, using the same procedure as in Example 2. $^1$H NMR (400 MHz, DMSO) δ 12.73 (bs, 1H), 11.60 (bs 1H), 7.93 (dd, J=6.3 Hz, 2.0 Hz, 1H), 7.78 (m, 1H), 7.39 (t, J=7.5 Hz, 1H), 7.29 (s, 1H), 6.91 (s, 1H), 4.26 (bs, 2H), 3.61 (bm, 4H), 2.42 (bm, 4H), 2.27 (s, 3H). Mass spectrum (LCMS, ESI pos.): Calcd for $C_{23}H_{20}N_6O_3BrF$: 527.4. Found: 527.0/529.0 (M+H).

c) (3-Amino-benzo[d]isoxazol-5-yl)-acetic acid [4-bromo-6-(4-methyl-piperazine-1-carbonyl)-2-oxo-1,2-dihydro-indol-3-ylidene]-hydrazide

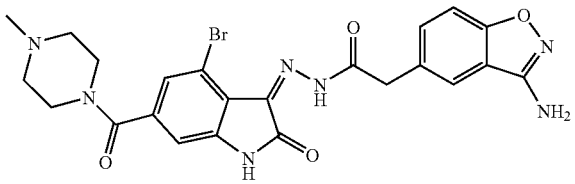

The product of the preceding step (0.057 g, 0.108 mmol), acetohydroxamic acid (0.042 g, 0.559 mmol), and powdered potassium carbonate (0.119 g, 0.863 mmol) were dissolved in 5 mL of anhydrous DMF under argon and heated to 50° C. under rubber septum for 24 h. The crude was purified twice by preparative TLC on silica gel (first with 15% MeOH/DCM, then with 20% MeOH/DCM, saturated with ammonia), then by HPLC (10-90% MeCN in water with 0.1% TFA over 30 min, on a semi-prep C8 Betasil column), giving the title compound as a yellow solid. $^1$H NMR (400 MHz, CDCl$_3$/CD$_3$OD) δ 7.70 (s, 1H), 7.60 (d, J=8.6 Hz, 1H), 7.35 (m, 2H), 6.99 (s, 1H), 4.35 (s, 2H), 3.92 (bm, 4H), 3.30 (bm, 4H), 2.91 (s, 3H). Mass spectrum (LCMS, ESI pos.): Calcd for $C_{23}H_{22}N_7O_4Br$: 540.4. Found: 539.9/541.9 (M+H).

Biological Activity

In Vitro Assays

The following representative in vitro assays were performed in determining the biological activities of compounds within the scope of the invention. They are given to illustrate the invention in a non-limiting fashion.

EXAMPLE A

Cloning, Expression, and Purification of Recombinant c-Met Protein

This example describes the cloning, expression, and purification of the cytoplasmic domain of c-Met which has the c-Met receptor tyrosine kinase activity. The cytoplasmic domain has 435 amino acids and shows high homology with the SRC family of tyrosine kinases (Park et al., 1987, Proc Natl Acad Sci USA. 84(18):6379-83).

A cDNA for the cytoplasmic domain of Met receptor, containing the tyrosine kinase domain, was amplified by PCR. Oligonucleotides were custom synthesized by Gibco-BRL (Carlsbad, Calif.). Forward oligonucleotide metkinF2 is identical to nucleotides 3068-3097 of the nucleotide sequence listed in NM_000245, except that nucleotides between 3073 and 3078 have been altered to create a BamHI site for cloning purposes. Reverse oligonucleotide metkinR2a is identical to nucleotides 4378-4348 of the complementary sequence of that listed in NM_000245 except that nucleotides between 4372-4367 have been altered to create a XhoI site (underlined) for cloning purposes. The oligonucleotides were used as PCR primers to amplify Met receptor cytoplasmic domain cDNA from Quick Clone placental cDNA (Clontech; Palo Alto, Calif.). Amplification was performed using Taq DNA polymerase (Gibco-BRL; Carlsbad, Calif.), 1.25 mM each dNTP, 200 nM each oligo, in a 50 µl volume. The thermocycle profile was 30 cycles of each containing 94° C. for 30 seconds, 60° C. for 30 seconds, and 72° C. for 1 minute, on a Perkin Elmer 9600 thermocycler.

The amplified cDNA for the cytoplasmic domain of Met receptor was cloned onto an expression vector. The PCR product was digested with BamHI (New England Biolabs; Beverly, Mass.) and XhoI (New England Biolabs). A digested 1.3 kb product was isolated and purified from a 1% agarose gel using Gene Clean (Qbiogene; Irvine, Calif.). Vector pFastBacHTa (Gibco-BRL) was digested with BamHI and XhoI (New England Biolabs) and the 4.7 kb linear fragment was purified from a 1% agarose gel using Gene Clean (Bio101). The 1.3 kb Met cDNA fragment was ligated to pFastBacHTa vector at 4° C. for 16 hours with T4 DNA ligase (New England Biolabs) in a final volume of 10 µl. Cloning the Met cytoplasmic domain cDNA clone into the BamHI site of pFastBacHTa placed the cDNA in-frame with the His-6 tag of the vector to allow for expression of an N-terminal His-tagged protein. Half the ligation mix (5 µL) was used to transform 50 µl DH5α competent *E. coli* cells (Gibco-BRL). The transformation mix was plated onto LB agarose plates containing 100 µg/ml ampicillin and incubated for 16 hours at 37° C. Colonies were picked from these plates and grown in LB broth containing 100 µg/ml ampicillin for 16 hours. Plasmid DNA was isolated using Qiagen plasmid DNA purification reagents (Qiagen; Valencia, Calif.) and clones screened by digest with BamHI/XhoI. Three clones which had the appropriate size fragment released from the digest were submitted to ACGT, Inc for DNA sequence analysis.

One clone, pFastBacHTmetkin-15, contained no mutations in the cloned c-Met cytoplasmic domain was used to generate a recombinant baculovirus for expression. Recombinant baculovirus was generated using the Gibco BRL Bac-To-Bac system following the protocol specified by the manufacturer. Briefly, DH10Bac cells were transformed with pFastBacHTmetkin-15, clones were selected, viral DNA isolated, and screened by PCR for Met cDNA insert. Sf9 insect cells were transfected with the recombinant baculovirus DNA. Media containing P0 viral stock was collected and used for 2 subsequent rounds of viral amplification.

Multiple concentrations of amplified viral stock were used to infect Sf9 cells. Cells were harvested 24, 48, and 72 hours post transfection. Infected Sf9 cells were lysed in 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin and total protein concentration determined in a BCA assay (Pierce; Rockford, Ill.). Cell lysates were separated on a 4-15% SDS-PAGE then transferred to nitrocellulose membrane for immunoblot analysis. Nitocellulose blots were probed with an anti-His6 antibody to confirm expression of the His-tagged met kinase protein. Optimal viral concentration to Sf9 cell ratio was determined by examination of lysates collected from different infection conditions. Maximal protein recovery occurred 48 hours post infection.

A small-scale expression/purification of the His-tagged cytoplasmic domain of Met receptor was performed. Sf9 insect cells transfected with the recombinant baculovirus that expresses the His-tagged cytoplasmic domain of Met receptor were lysed in buffer containing 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin. The lysate was incubated with 5 ml of a 50% solution of Ni-agarose beads (Qiagen) in PBS for 2 hours rotating at 4° C. to capture the His-tagged protein. The lysate containing His-tagged protein bound to Ni-agarose beads was loaded onto a 10 ml column. Ni-agarose beads were allowed to pack and supernatant allowed to flow through. The packed column was then washed with 60 ml of wash buffer (same as lysis buffer). 5 ml of elution buffer (50 mM Tris-HCl pH 8, 150 mM NaCl, 150 mM imidazole, 1.0 mM PMSF) was added to the column and 10 fractions (0.5 ml volume each) were collected. Small aliquots of each fraction were separated by 4-15% SDS-PAGE and either transferred to nitrocellulose for immunoblot analysis or processed for Coomassie stain (Bio-Safe Safe Coomassie, Bio-Rad). The major protein band on the Coomassie stain gel has the appropriate size for His6-MetKin (52 kD), corresponding to the His-tagged protein detected by immunoblot. Protein concentration as estimated from the Coomassie stain gel was approximately 2 mg/ml.

Recombinant viral stock was transferred to the contract lab, Pan Vera (Madison, Wis.) for large-scale expression and purification of His6-MetKin in quantities sufficient for High Throughput Screening. A 60 L scale up and 4 step purification scheme yielded 98.4 mg of protein that is more than 95% pure.

EXAMPLE B

Delfia Autophosphorylation Kinase Assay on the c-Met

A DELFIA time resolved fluorescence assay was developed for screening of compounds that decreases the autophosphorylation thus the kinase activity of c-Met.

The DELFIA assay is non-radioactive. The autophophorylation of the c-Met is measured by an anti-phosphotyrosine antibody coupled to an Europium tag.

A major advantage of this format is that it allowed for the development of an autophosphorylation assay using Ni-chelate plates which bind the hexa-his tag on the recombinant Met kinase. Autophosphorylation assay allows to use a known substrate, Met kinase itself, for the phosphorylation. The DELFIA Met autophosphorylation assay is very sensitive with a signal to noise ratio in excess of 50:1.

The assay procedure for screening is as follows. The purified His6 tagged cytoplasmic domain of c-Met was diluted to a concentration of 500 ng/ml in enzyme dilution buffer (50 mM Tris-HCl, pH8.0, 0.1% BSA) and dispensed to assay plates at a volume of 50 µl per well. Black opaque HisGrab Nickel coated 96 well plates (Pierce, Rockford, Ill.) were selected to run the assay. Next, 2.5 µl of compound in 40% DMSO was added to test wells, 2.5 µl of 40% DMSO only was added to the negative control wells. The autophosphorylation reaction was initiated upon the addition of 50 µl of reaction buffer, 50 mM Tris-HCl, pH 8.0, 10 mM $MgCl_2$, 0.1 mM $Na_3VO_4$, 1 mM DTT, 1 µM ATP. Plates were incubated at room temperature for 1 hour followed by 2 washes with 200 µl/well of PBS. Europium conjugated anti-phosphotyrosine antibody, Eu-PY20 from Perkin Elmer was diluted to 50 ng/ml in Delfia AB buffer (Perkin Elmer, Boston, Mass.), added to the 96 well assay plates at a volume of 1001 µl/well, and incubated at room temperature for 2 hours. Assay plates were then washed 4 times each with 200 µl/well of Delfia wash buffer (Perkin Elmer). After the final wash 150 µl of Delfia Enhancement solution (Perkin Elmer) was added to each well of the assay plate and incubated at room temperature for 1 hour. Plates were read on an LJL Analyst instrument (Molecular Devices; Sunnyvale, Calif.) with filter settings of 360 excitation, 620 emission, and 410 dichroic. $IC_{50}$ values were calculated using Graphpad Prism software (Graphpad Software; San Diego, Calif.).

EXAMPLE C

Fluorescence Polarization Assay on the Kinase Activity of c-Met

A fluorescence polarization assay (FP) was developed for screening of compounds that decreases the kinase activity of c-Met.

A protein (6H-TEV-cMet) comprising c-Met kinase domain was cloned, recombinantly expressed and purified following a procedure similar to that as described in Example A. The protein comprises a His tag consisting of six histidines at its N-terminal, a TEV protease cleavage site, and the c-Met kinase domain. The c-Met kinase domain consists amino acid 1046-1390 of the c-Met protein as listed in GenBank protein accession number P08581.

For the c-Met kinase assay, the 6H-TEV-cMet was used as the enzyme, and a poly $Gly_4Tyr$ peptide (Sigma, P-0275) was used as the substrate. The kinase reaction was performed in a volume of 10 µl in HE microplates (LJL Biosystems). Assay conditions were as follows: 100 mM HEPES pH 7.5, 0.01% Tween-20, 1 mM DTT, 5 mM $MgCl_2$, 10 µM ATP, 10 µg/ml poly $Gly_4Tyr$. The kinase reaction was initiated upon addition of 10 nM 6H-TEV-cMet. After a 12 minute incubation at room temperature the reaction was terminated with 1.2 of 50 mM EDTA.

Phosphorylation of the peptide substrate was detected with PanVera Tyrosine Kinase Assay Kit, Green reagents (P2837). Five minutes after the addition of EDTA, 10 µl of antibody/tracer mix (Pan Vera reagents, 1:1:3 dilution of antibody: Tracer: FP dilution buffer, Cat. # P2837) was added to each well. Plates were allowed to incubate for 30 minutes at room temperature and fluorescence polarization was measured with an LJL Analyst instrument (Molecular Devices; Sunnyvale, Calif.) with excitation=485 nm filter and emission=530 nm filter. $IC_{50}$ values were calculated from triplicate sets of data using Graphpad Prism software (Graphpad Software; San Diego, Calif.).

EXAMPLE D

A Cell Based ELISA Assay for c-Met Phosphorylation

A cell based ELISA assay was developed to evaluate the ability of compounds to inhibit HGF stimulated c-Met phosphorylation in cells.

S114 cells were seeded to a 96 well tissue culture treated dish at a concentration of $5 \times 10^4$ per well. After a 16-20 hour incubation, culture medium was removed and replaced with serum free medium supplemented with 0.5% BSA. Test compound was then added and incubated with the cells for 60 minutes, followed by the addition of 1 µl HGF at 2.5 µg/µl for 15 minutes. Cells were then lysed with the addition of 25 µl of ice cold 3× RIPA buffer (50 mM Tris HCl, pH 7.5, 1% Triton, 1% IGEPAL, 0.25% deoxycholic acid, 150 mM NaCl, 1 mM sodium orthovanidate, 1 mM sodium fluoride, and 1 tablet protease cocktail inhibitor (Boheringer Mannheim, cat. #1697498). Cell lysates were then transferred to NUNC Maxisorp plates coated with anti-c-Met receptor antibody AF276 (R&D Systems). Lysates were incubated with the antibody-coated plates for 1 hour at room temperature. Plates were washed with Delfia wash buffer (Perkin Elmer, Boston, Mass.) and 100 µl of 0.25 ug/ml europium conjugated PT66 anti-phosphotyrosine antibody (Perkin Elmer, Boston, Mass.). Following another 1 hour incubation at room temperature the plates were washed three times with Delfia wash buffer (Perkin Elmer). After the final wash, 150 ml of Delfia enhancer solution (Perkin Elmer) was added and allowed to incubate for 60 minutes. Plates were read on an LJL Analyst instrument (Molecular Devices; Sunnyvale, Calif.) with filter settings of 360 excitation, 620 emission, and 410 dichroic. $IC_{50}$ values were calculated using Graphpad Prism software (Graphpad Software; San Diego, Calif.).

Aqueous Solubility Assay

Compounds of the present invention were tested for aqueous solubility in order to obtain optimal solubility without adversely affecting the potency of the compound. Aqueous solubility was determined in the following manner: Compounds were taken from a 10 mM DMSO (dimethyl sulfoxide) stock solution and diluted in water, PBS (phosphate buffered saline), aqueous HCl at pH2 and DMSO. Water, PBS and aqueous HCl at pH2 having a final DMSO content of 0.4%, with the final DMSO concentration reaching 40 µM. Samples were placed in the incubator and shaken for 15 minutes. Aqueous solubility was then determined by LC/MS under the following conditions:

Mobile Phase A: 0.05% $CF_3CO_2H$ + 5.0% $CH_3CN$ in $H_2O$
Mobile Phase B: 0.05% $CF_3CO_2H$ in $CH_3CN$
Gradient: 5-95% B in 2.5 minutes
Run Time: 3.1 min
Flow Rate: 0.4 ml/min
Injection Volume: 15-30 µL (as needed)
Column: Princeton Chromatography, PrincetonSPHER C30 200A 5u, 50×2.0 mm with 2.0×23 mm guard cartridges Solubility results were calculated under the assumption that compound solubility in DMSO is 100% at 40 µM.

In Vitro Biological Data

The activity of representative compounds of the present invention is presented in the chart below. All activities are in µM and data is accepted as valid if the 95% confidence intervals calculated by Graphpad prism are within 2 fold of the $IC_{50}$.

| Example Number | Structure | c-Met FP Enz IC50 µM | c-Met Delfia Autophos IC50 µM | Solubility in $H_2O$ (uM) |
|---|---|---|---|---|
| 1 | 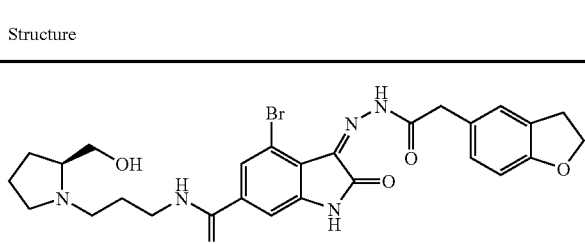 | 0.006 | | |
| 2 | 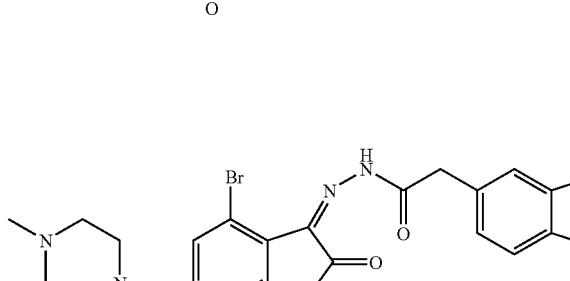 | 0.010 | | 43.85 |

-continued

| Example Number | Structure | c-Met FP Enz IC50 μM | c-Met Delfia Autophos IC50 μM | Solubility in H₂O (uM) |
|---|---|---|---|---|
| 3 | 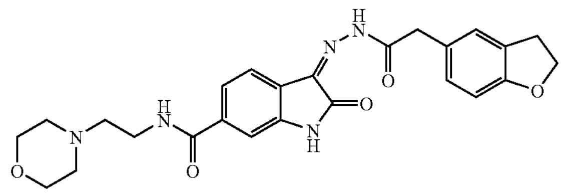 | 0.024 | 0.024 | 38.06 |
| 4 | 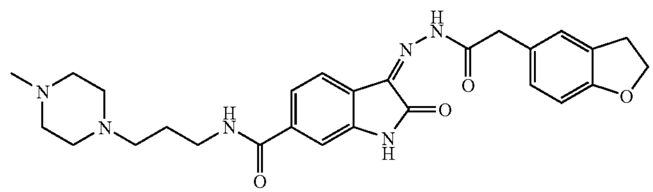 | | 0.028 | 37.9 |
| 5 | 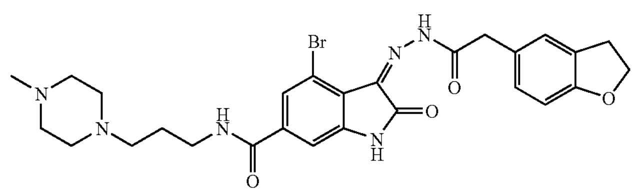 | 0.013 | 0.001 | 38.76 |
| 6 | 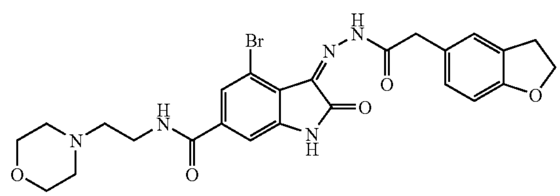 | 0.005 | 0.005 | 43.95 |
| 7 | 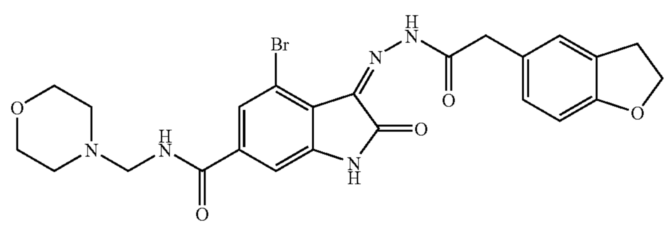 | 0.001 | 0.0007 | 42.74 |
| 8 | 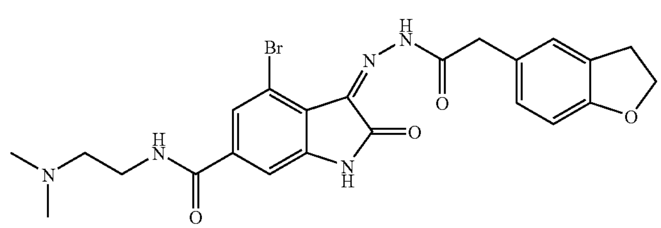 | 0.01 | 0.001 | 41.08 |
| 9 | 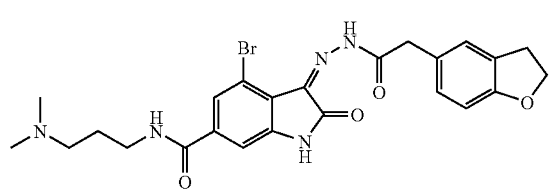 | | 0.005 | |

| Example Number | Structure | c-Met FP Enz IC50 μM | c-Met Delfia Autophos IC50 μM | Solubility in H₂O (uM) |
|---|---|---|---|---|
| 10 | 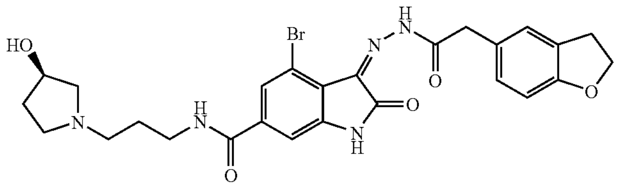 | | 0.0007 | |
| 11 | 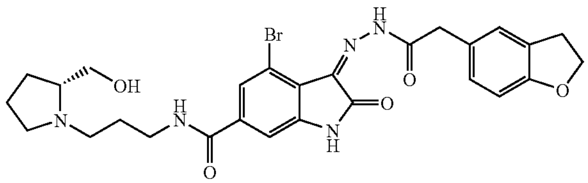 | | 0.0005 | |
| 12 | 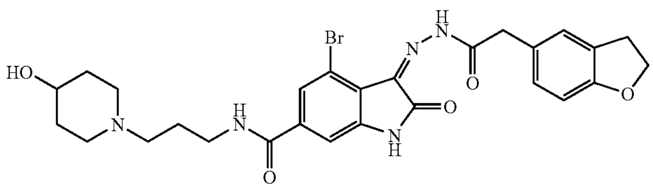 | | 0.002 | |
| 13 | 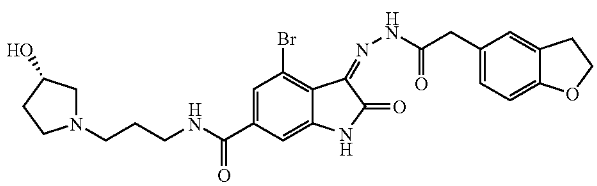 | | 0.001 | |
| 14 | 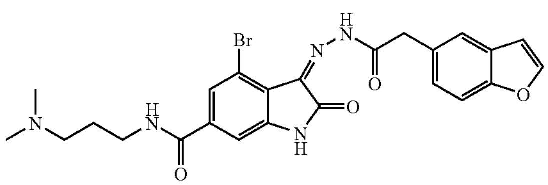 | | 0.0016 | |
| 15 | 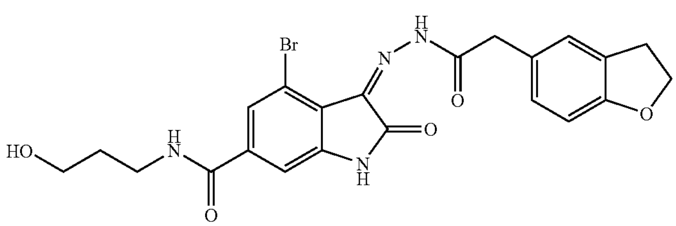 | | 0.001 | |
| 16 | 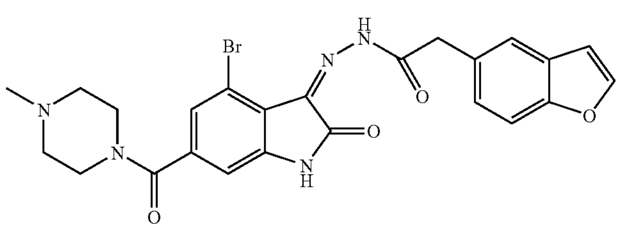 | | 0.065 | |

| Example Number | Structure | c-Met FP Enz IC50 µM | c-Met Delfia Autophos IC50 µM | Solubility in H$_2$O (uM) |
|---|---|---|---|---|
| 17 | 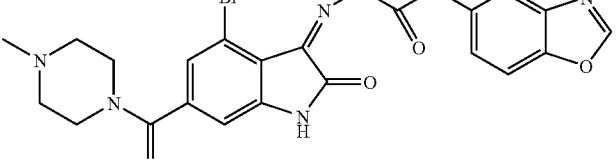 | | 0.656 | |
| 18 | 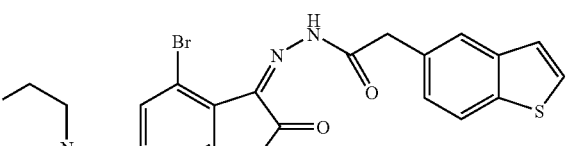 | | 4.70 | |
| 19 | 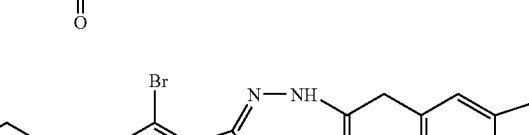 | | 0.158 | |

In Vivo Assays

The following representative in vivo assay was performed in determining the biological activities of compounds within the scope of the invention. They are given to illustrate the invention in a non-limiting fashion.

The anti-tumor efficacy of a subset of the compounds of the invention was evaluated in vivo using a nude mouse U87MG human tumor xenograft regression model.

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

The human glioblastoma U-87MG cell line was obtained from the American Type Culture Collection (ATCC Number: HTB-14) and propagated in minimum essential (Eagle) medium containing 2 mM L-glutamine, 1.5 g/L sodium bicarbonate, 0.1 mM non-essential amino acids, 1.0 mM sodium pyruvate, and 10% FBS (fetal bovine serum). U87MG cells express both c-Met and its ligand HGF, therefore strong anti-tumor activity against U87MG tumor growth in the nude mouse tumor xenograft model is anticipated to be a desirable quality of the invention.

In pilot growth studies, the following conditions were identified as permitting U87MG cell growth in nude mice as subcutaneous solid tumor xenografts: Immediately prior to injection, cells were washed in PBS and counted, suspended at a concentration of 1×10$^7$ cells/mL, and loaded into 1 cc syringes equipped with 25 gauge needles. Female athymic nude mice weighing no less than 20-21 grams were inoculated subcutaneously in the left inguinal region of the thigh with 1×10$^6$ tumor cells in a delivery volume of 0.1 mL. Tumors were allowed to grow to a pre-determined size prior to initiation of dosing. Approximately 2 weeks after tumor cell inoculation, mice bearing subcutaneous tumors were randomly assigned to treatment groups such that all treatment groups had similar starting mean tumor volumes of ~100 mm$^3$. Mice were dosed IP (intra-peritoneal) with vehicle (control group) or compound at various doses either twice-daily (b.i.d.) or once-daily (q.d.). Dosing was continued for 11 consecutive days, depending on the kinetics of tumor growth and size of tumors in vehicle-treated control mice. If tumors in the control mice reached ~10% of body weight (~2.0 grams), the study was to be terminated. Compounds of the present invention were prepared fresh daily as a clear solution (@ 1, 1.5 and 3 mg/mL) in 20% HPβCD and administered IP as described above. During the study, tumor growth was measured three times-a-week (M, W, F) using electronic Vernier calipers. Tumor volume (mm$^3$) was calculated using the formula (L×W)$^2$/2, where L=length (mm) and W=width (shortest distance in mm) of the tumor. Body weight was measured three times-a-week and a loss of body weight >10% was used as an indication of lack of compound tolerability. Unacceptable toxicity was defined as body weight loss >20% during the study. Mice were closely examined daily at each dose for overt clinical signs of adverse, drug-related side effects.

On the day of study termination, a final tumor volume and final body weight were obtained on each animal. Mice were euthanized using 100% $CO_2$ and tumors were immediately excised intact and weighed, with final tumor wet weight (grams) serving as a primary efficacy endpoint.

The time course of the inhibitory effects of compounds of the present invention on the growth of U87MG tumors is illustrated in FIG. 1. Values represent the mean (±sem) of 15 mice per treatment group. Percent inhibition (% 1) of tumor growth was calculated versus tumor growth in the vehicle-treated Control group on the last study day. Statistical significance versus Control was determined by Analysis of Variance (ANOVA) followed by Dunnett's t-test: * $p<0.05$. The 30 mpk (mg compound per kg animal weight) dosing group was terminated on day 3 due to treatment related deaths of 50% of the mice in the group. Dosing of the 15 mpk group was reduced from b.i.d. administration to q.d. administration on day 4 due to overt toxicity. The 10 mpk group continued to be dosed b.i.d throughout the course of the study except for days 6 and 7 which were administered q.d.

Figure 2:
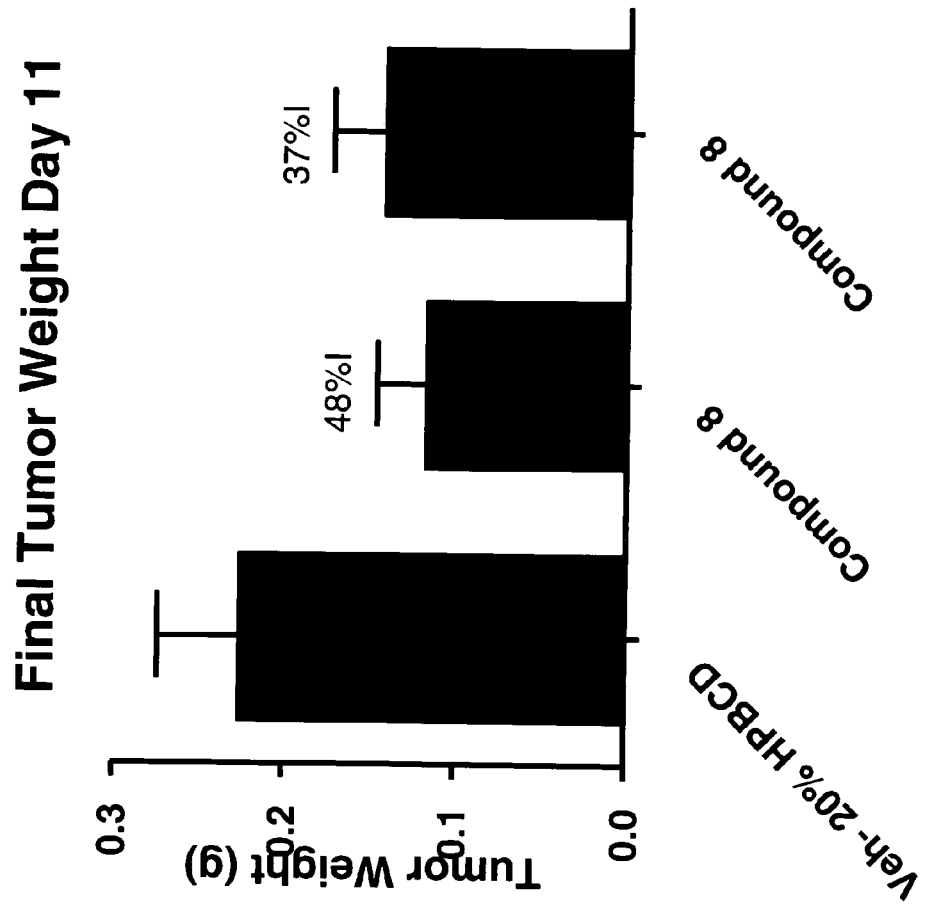
FIG. 2 shows shows the effects of oral administration of compounds of the present invention on the final weight of U87MG tumors xenografts in nude mice.

A similar reduction of final tumor weight was noted at study termination. (See FIG. 2). Values represent the mean (±sem) of 15 mice per treatment group. Percent Inhibition was calculated versus the mean tumor weight in the vehicle-treated control group. Statistical significance versus Control was not reached for either treatment group as determined by ANOVA followed by Dunnett's t-test analysis.

Methods of Treatment/Prevention

In another aspect of this invention, compounds of the invention can be used to inhibit tyrosine kinase activity or expression, including c-Met activity, reduce kinase activity or expression, including c-Met activity, and modulate expression of c-Met in a cell or a subject, or to treat disorders related to c-Met kinase activity or expression in a subject. Inhibition of c-Met activity is believed to indirectly modulate c-Met expression.

In one embodiment to this aspect, the present invention provides a method for reducing or inhibiting the kinase activity of c-Met, and modulate expression of c-Met in a cell comprising the step of contacting the cell with a compound of Formula I. The present invention also provides a method for reducing or inhibiting the kinase activity of c-Met, and modulate expression of c-Met in a subject comprising the step of administering a compound of Formula I to the subject. The present invention further provides a method of inhibiting cell proliferation in a cell comprising the step of contacting the cell with a compound of Formula I.

The kinase activity or expression of c-Met in a cell or a subject can be determined by procedures well known in the art, such as the c-Met kinase assay described herein. Inhibition of c-Met kinase activity in cells can also be measured by determining the level of c-Met phosphorylation using an ELISA assay format such as the one described here.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to c-Met. Such disorders include pre-existing conditions related to c-Met expression (or over expression) and/or c-Met mutation.

In one example, the invention provides methods for preventing in a subject a cell proliferative disorder or a disorder related to c-Met, comprising administering to the subject a prophylactically effective amount of a pharmaceutical composition comprising the compound of Formula I and a pharmaceutically acceptable carrier. Administration of said prophylactic agent can occur prior to the manifestation of symptoms characteristic of the cell proliferative disorder or disorder related to c-Met, such that a disease or disorder is prevented or, alternatively, delayed in its progression.

In another example, the invention pertains to methods of treating in a subject a cell proliferative disorder or a disorder related to c-Met comprising administering to the subject a therapeutically effective amount of a pharmaceutical composition comprising the compound of Formula I and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to c-Met.

In another example, the invention pertains to methods of modulating in a subject a cell proliferative disorder or a disorder related to c-Met, such that modulation of the level of c-Met expression or of c-Met activity may act to ameliorate the cell proliferative disorder or a disorder related to c-Met, comprising administering to the subject a therapeutically effective amount of a pharmaceutical composition comprising the compound of Formula I and a pharmaceutically acceptable carrier.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to c-Met", or "disorders related to c-Met receptor tyrosine kinase" shall include diseases associated with or implicating c-Met activity, for example, the overactivity of c-Met, and conditions that accompany with these diseases. The term "overactivity of c-Met" refers to either 1) c-Met expression in cells which normally do not express c-Met; 2) c-Met expression by cells which normally do not express c-Met; 3) increased c-Met expression leading to unwanted cell proliferation; or 4) mutations leading to constitutive activation of c-Met. Examples of "disorders related to c-Met" include disorders resulting from over stimulation of c-Met due to abnormally high amount of c-Met or mutations in c-Met, or disorders resulting from abnormally high amount of c-Met activity due to abnormally high amount of c-Met or mutations in c-Met.

It is known that overactivity of c-Met has been implicated in the pathogenesis of a number of diseases, such as cell proliferative disorders, neoplastic disorders and cancers.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. Cell proliferative disorders include neoplastic disorders (as used herein, a "neoplastic disorder" refers to a tumor resulting from abnormal or uncontrolled cellular growth) and other cell proliferative disorders.

Examples of cell proliferative disorders related to c-Met, include tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelima, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—including leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma)—and diseases associated with the formation of new vasculature, such as rheumatoid, arthritis, retinopathy.

Other cell proliferative disorders in which overactivity of c-Met has been implicated in their pathogenesis include cancers in which c-Met activity contributes to the invasive/metastatic phenotype, including cancers in which c-Met is not overexpressed or otherwise altered.

In a further embodiment to this aspect, the invention encompasses a combination therapy for treating or inhibiting the onset of a cell proliferative disorder or a disorder related to c-Met in a subject. The combination therapy comprises administering to the subject a therapeutically or prophylactically effective amount of a compound of Formula I, and one or more other anti-cell proliferation therapy including chemotherapy, radiation therapy, gene therapy and immunotherapy.

In an embodiment of the present invention, the compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine); alkylating agents (e.g., cyclophosphamide, carmustine, lomustine, thiotepa); epipodophyllotoxins/podophyllbtoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, carminomycin, daunomycin); anti-metabolites (e.g., clofarabine, aminopterin, cytosine arabinoside, methotrexate); tubulin-binding agents (e.g. combretastatin, colchicine, nocodazole); topoisomerase inhibitors (e.g., camptothecin). Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6):449-67. Additionally, yet to emerge chemotherapeutic agents are contemplated as being useful in combination with the compound of the present invention.

In another embodiment of the present invention, the compound of the present invention may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

By way of example only, camptothecin compounds are advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

By way of example only, vinca alkaloids may be advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

By way of example only, anti-tumor nucleoside derivatives may be advantageously administered in a dosage of 200 to 2500 mg per square meter (mg/m$^2$) of body surface area, for example 700 to 1500 mg/m$^2$. 5-fluorouracil (5-FU) is commonly used via intravenous administration with doses ranging from 200 to 500 mg/m$^2$ (preferably from 3 to 15 mg/kg/day). Gemcitabine is advantageously administered in a dosage of about 800 to 1200 mg/m$^2$ and capecitabine is advantageously administered in about 1000 to 2500 mg/m$^2$ per course of treatment.

By way of example only, alkylating agents may be advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg of body weight, for carmustine in a dosage of about 150 to 200 mg/m$^2$, and for lomustine in a dosage of about 100 to 150 mg/m$^2$ per course of treatment.

By way of example only, podophyllotoxin derivatives may be advantageously administered in a dosage of 30 to 300 mg per square meter (mg/m2) of body surface area, for example 50 to 250 mg/m$^2$, particularly for etoposide in a dosage of about 35 to 100 mg/m$^2$ and for teniposide in about 50 to 250 mg/m$^2$ per course of treatment.

By way of example only, anthracycline derivatives may be advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m$^2$) of body surface area, or as known in the art, if different. For example, trastuzumab is advantageously administered in a dosage of 1 to 5 mg/m$^2$ particularly 2 to 4 mg/m$^2$ per course of treatment.

Dosages may be administered, for example once, twice or more per course of treatment, which may be repeated for example every 7, 14, 21 or 28 days.

The compounds of the present invention can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving.

The compounds of the present invention can further be administered to a subject in combination with a targeting agent to achieve high local concentration of the compound at the target site. In addition, the compounds of the present invention may be Formulated for fast-release or slow-release with the objective of maintaining the drugs or agents in contact with target tissues for a period ranging from hours to weeks.

The present invention also provides a pharmaceutical composition comprising a compound of Formula I in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" Formulations include Formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release Formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of a compound of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of this invention. The compound of Formula I, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preFormulation composition containing a homogeneous mixture of a compound of the present invention, or a pharmaceutically acceptable salt thereof. When referring to these preFormulation compositions as homogeneous, it is meant that the active ingredient is dispersed evenly throughout the composition so that the composition may be readily subdivided into equally effective dosage forms such as tablets, pills and capsules. This solid preFormulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compound of Formula I may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of Formula I may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compound of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compounds of the present invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administer.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds which prevent inflammation and proliferation, may provide the most efficacious treatment for post-angioplasty restenosis.

Compounds of the invention can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent which makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compounds of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restenosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis. See Schiele T M et. al., 2004, "Vascular restenosis—striving for therapy." Expert Opin Pharmacother. 5(11): 2221-32. Vascular smooth muscle cells (VSMC) express c-Met receptor. Exposure to hepatocyte growth factor, the ligand for c-Met, stimulates these cells to exhibit a migratory phenotype. See Taher et. al., Hepatocyte growth factor triggers signaling cascades mediating vascular smooth muscle cell migration. *Biochem Biophys Res Commun.* (2002) 298 (1):80-6; Morishita R, Aoki M, Yo Y, Ogihara T. Hepatocyte growth factor as cardiovascular hormone: role of HGF in the pathogenesis of cardiovascular disease. Endocr J. (2002) June; 49(3):273-84. Since VSMC migration from the media to the intima of arteries plays a role in the development of atherosclerosis and restenosis, antagonists of c-Met kinase activity are believed to present a viable therapeutic strategy in the treatment of these diseases.

Accordingly, the present invention provides a method for the treatment of disorders related to c-Met, including restenosis, intimal hyperplasia or inflammation, in blood vessel walls, comprising the controlled delivery, by release from an intraluminal medical device, such as a stent, of a compound of the invention in therapeutically effective amounts.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal. In the present invention, the targetable or accessible component might be the c-Met receptor as it is accessible and expressed on or near the target tissues.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No. 5,855,866 to Thorpe et al). Methods are known to those skilled in the art to produce and isolate antibodies against tumor (U.S. Pat. No. 5,855,866 to Thorpe et al., and U.S. Pat. No. 6,34,2219 to Thorpe et al.).

Techniques for conjugating therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53. (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolyzable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target-site.

The present invention provides a pharmaceutical composition comprising an effective amount of a compound of the present invention conjugated to a targeting agent and a pharmaceutically acceptable carrier.

The present invention further provides a method of treating of a disorder related to c-Met, particularly a tumor, comprising administering to a subject a therapeutically effective amount of a compound of Formula I conjugated to a targeting agent.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the compound of the present invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula I:

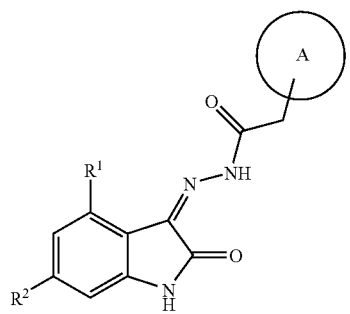

Formula I pharmaceutically acceptable salts, N-oxides, and stereochemical isomers thereof, wherein:
A is selected from:

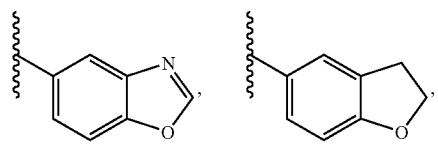

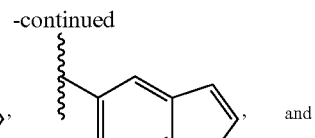
-continued and the A ring being optionally substituted with —$NH_2$, —$CH_3$, —$CF_3$, —$NO_2$, -CN, Cl, F, or Br;
$R^1$ hydrogen or halogen;
$R^2$ is selected from the group consisting of Formula II, Formula III or Formula IV;

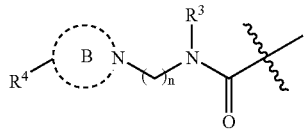

Formula II

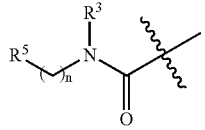

Formula III

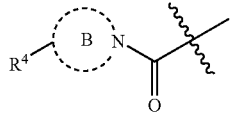

Formula IV wherein n is 2, 3 or 4;
B is a nitrogen containing heterocyclic ring;
$R^3$ is hydrogen or alkyl;
$R^4$ is H, alkyl, hydroxyalkyl, hydroxyl, or —C(O)alkyl; and
$R^5$ is OH, NH-alkyl, N-alkyl$_2$, or $NH_2$.

2. A compound of claim 1, wherein:
$R^1$ is hydrogen, Cl or Br;
A is selected from:

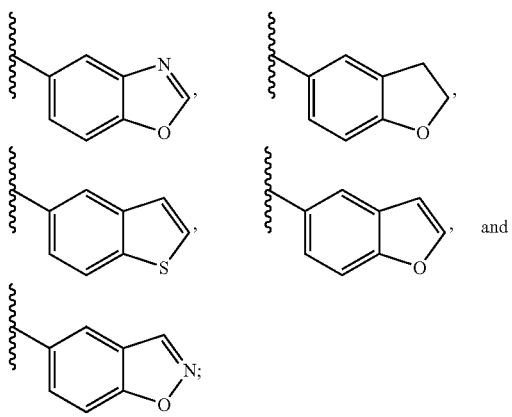

and and

R² is Formula II wherein:
  n is 2 or 3;
  B is morpholinyl, piperidinyl, piperazinyl, or pyrrolidinyl;
  R³ is hydrogen; and
  R⁴ is hydrogen, hydroxyl, hydroxymethyl, methyl, ethyl, propyl or isopropyl.

3. A compound of claim 2, wherein:
A is

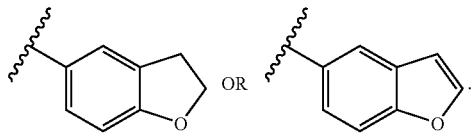

4. A compound of claim 1, wherein:
R¹ is hydrogen, Cl or Br;
A is

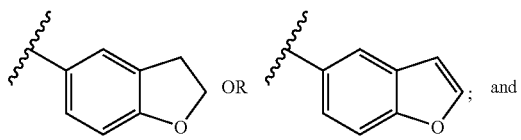

R² is Formula III wherein
n is 2 or 3;
R³ is hydrogen; and
R⁵ is hydroxyl, methylamino, ethylamino, propylamino, isopropylamino, dimethylamino, diethylamino, dipropylamino, methylethylamino, or methylpropylamino.

5. A compound of claim 1, wherein:
R¹ is hydrogen, Cl or Br;

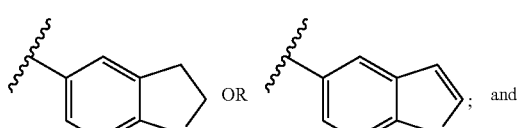

A is
R² is Formula IV wherein:
  B is morpholinyl, piperidinyl, piperazinyl, or pyrrolidinyl; and
  R⁴ is hydrogen, hydroxyl, hydroxymethyl, methyl, ethyl, propyl or isopropyl.

6. A compound of claim 1, wherein:
R¹ is hydrogen, Cl or Br;

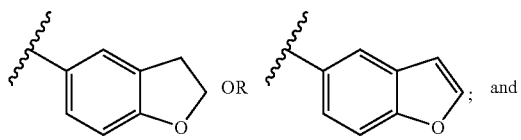

A is
R² is Formula III wherein:
  n is 2 or 3;
  R³ is hydrogen; and
  R⁵ is hydroxyl, dimethylamino, diethylamino, or dipropylamino.

7. A compound of claim 1, wherein
R¹ is hydrogen, Cl or Br;

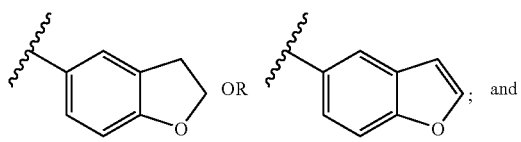

A is
R² is Formula IV wherein:
  B is piperazine; and
  R⁴ is hydrogen, methyl, ethyl, propyl or isopropyl.

8. A pharmaceutical composition comprising a compound of claim 1 and a pharmaceutically acceptable carrier.

9. A combination of a chemotherapeutic agent and a compound as claimed in claim 1.

10. A compound selected from the group consisting of:

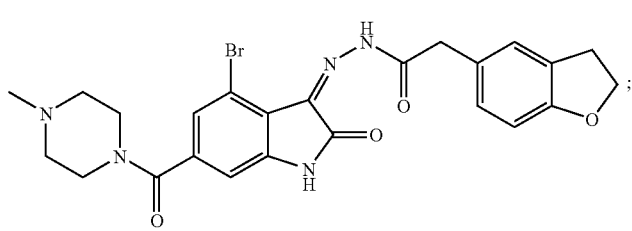

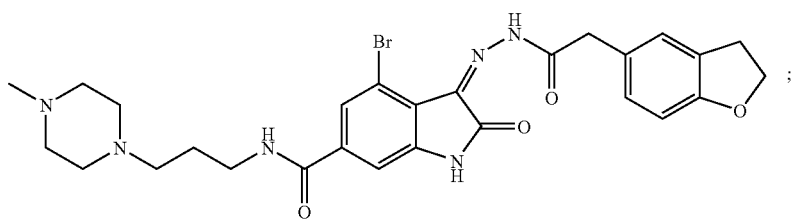

-continued
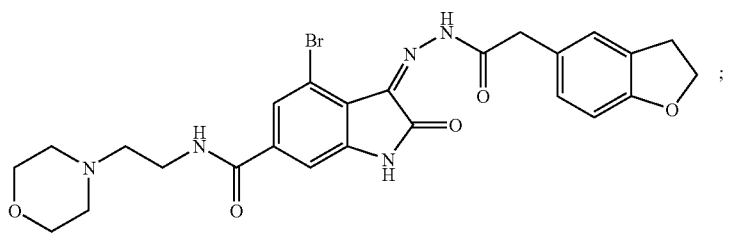;
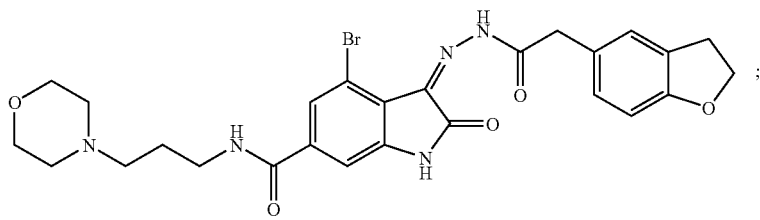;
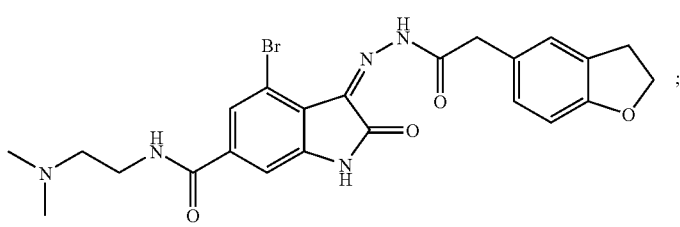;
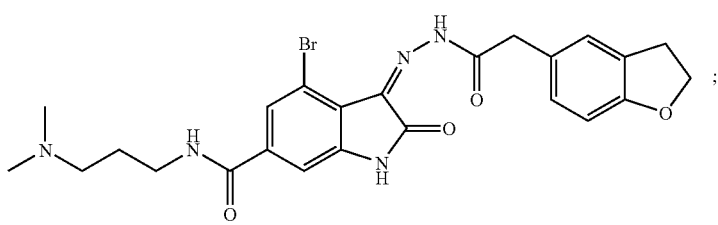;
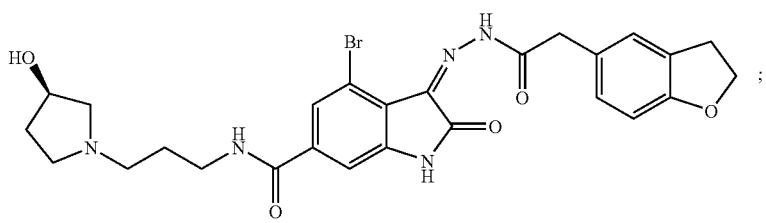;
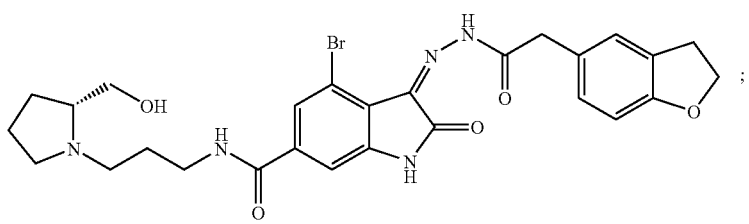;
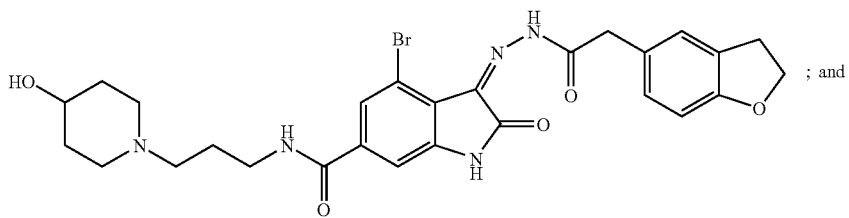; and -continued
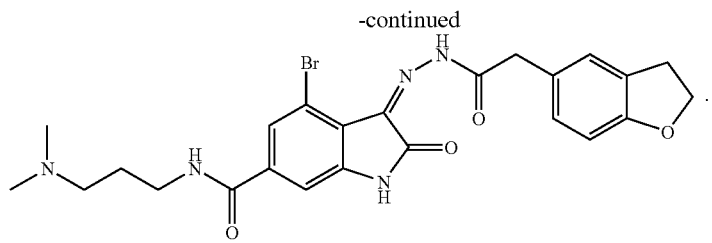
11. A compound selected from the group consisting of:
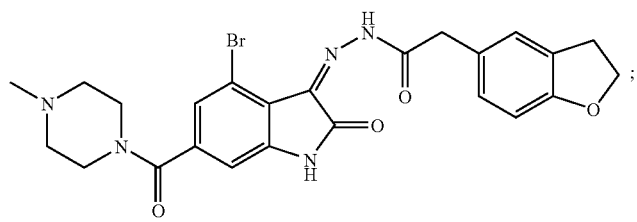;
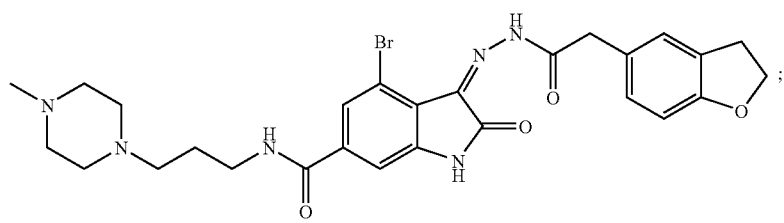;
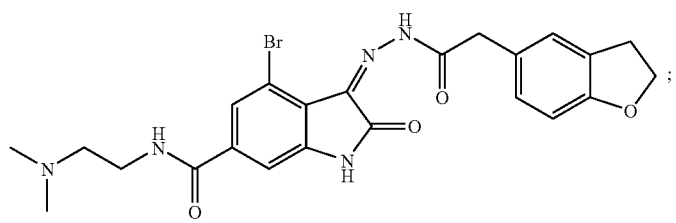;
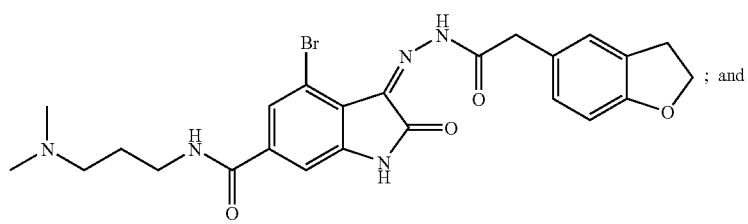; and -continued
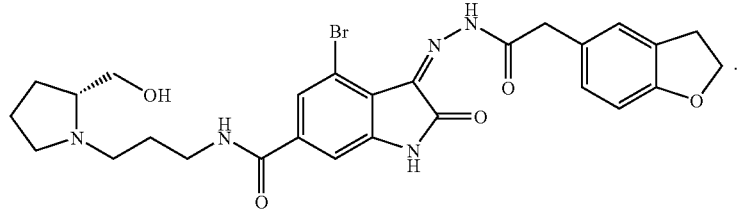
12. A compound selected from the group consisting of:
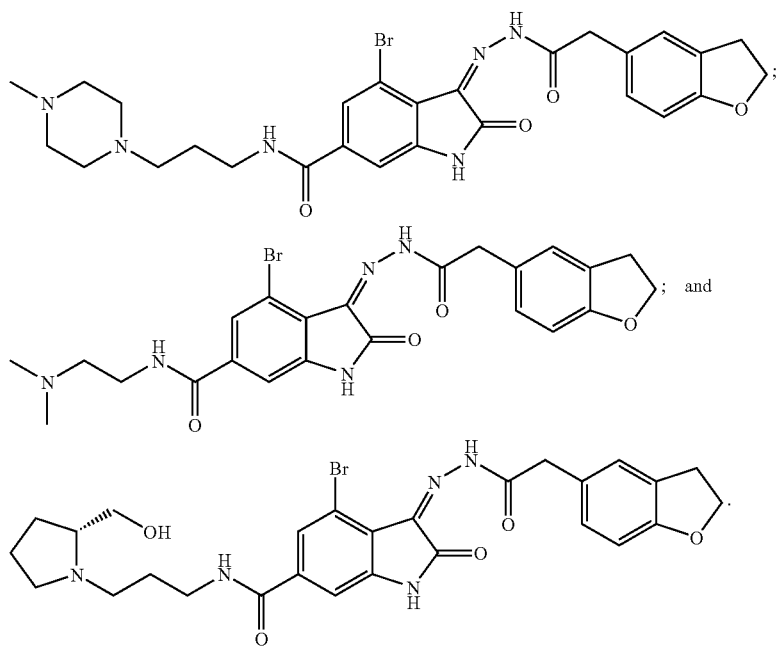
* * * * *